United States Patent
DiMauro et al.

(10) Patent No.: US 8,267,883 B2
(45) Date of Patent: Sep. 18, 2012

(54) PHOTOCATALYTIC IMPLANT HAVING A SENSOR

(75) Inventors: Thomas M. DiMauro, Raynham, MA (US); Jeffrey K. Sutton, Raynham, MA (US); Mohamed Attawia, Holmdel, NJ (US); Hassan Serhan, Raynham, MA (US); John Daniel Malone, Raynham, MA (US); Timothy Beardsley, Raynham, MA (US)

(73) Assignee: DePuy Spine, Inc., Raynham, MA (US)

( * ) Notice: Subject to any disclaimer, the term of this patent is extended or adjusted under 35 U.S.C. 154(b) by 63 days.

(21) Appl. No.: 12/817,585

(22) Filed: Jun. 17, 2010

(65) Prior Publication Data

US 2010/0317948 A1    Dec. 16, 2010

Related U.S. Application Data

(63) Continuation-in-part of application No. 10/774,105, filed on Feb. 6, 2004, now Pat. No. 7,744,555.

(51) Int. Cl.
  *A61M 5/00*  (2006.01)
  *A61N 1/30*  (2006.01)
  *A61F 2/00*  (2006.01)
  *A62B 7/08*  (2006.01)

(52) U.S. Cl. .............. 604/8; 604/20; 604/501; 424/423; 422/122

(58) Field of Classification Search ............... 604/8, 20, 604/501, 174, 180, 96.01, 890.1; 422/139, 422/122; 424/423
See application file for complete search history.

(56) References Cited

U.S. PATENT DOCUMENTS

| | | | |
|---|---|---|---|
| 4,344,438 A | 8/1982 | Schultz |
| 4,387,715 A | 6/1983 | Hakim |
| 4,551,128 A | 11/1985 | Hakim |
| 4,560,375 A | 12/1985 | Schulte |
| 4,595,390 A | 6/1986 | Hakim |
| 4,615,691 A | 10/1986 | Hakim |
| 4,772,257 A | 9/1988 | Hakim |
| 4,816,016 A | 3/1989 | Schulte |
| 4,832,034 A | 5/1989 | Pizziconi |
| 4,861,484 A | 8/1989 | Lichtin |
| 4,950,232 A | 8/1990 | Ruzicka |

(Continued)

FOREIGN PATENT DOCUMENTS

JP         10277144         10/1998

(Continued)

OTHER PUBLICATIONS

Akin, "Preparation and analysis of macroporous Ti02 films on Ti surfces for bone-tissue implants", J. Biomed. Mat. Res., 2001, pp. 588-596, vol. 57.

(Continued)

*Primary Examiner* — Jacqueline F. Stephens

(57) ABSTRACT

An implant comprises a photocatalytic layer on at least one surface and is adapted to act as a sensor. In some embodiments, the photocatalytic layer is a semiconductor oxide that is doped. According to some embodiments, the implant comprises a wave guide. According to some embodiments the implant comprises a light port. According to some embodiments, the implant comprises a reflective material on a surface of the waveguide. According to some embodiments the implant comprises a composite material comprising a first material that has a transmissivity when exposed to a predetermined wavelength of light and a second material that has photocatalytic activity when exposed to the predetermined wavelength of light. According to some embodiments the implant comprises a light source adapted to irradiate the photocatalytic surface.

4 Claims, 21 Drawing Sheets

U.S. PATENT DOCUMENTS

| | | | |
|---|---|---|---|
| 5,176,627 | A | 1/1993 | Watson |
| 5,385,541 | A | 1/1995 | Kirsch |
| 5,712,229 | A | 1/1998 | Hopkins |
| 5,738,666 | A | 4/1998 | Watson |
| 5,779,912 | A | 7/1998 | Gonzalez Martin |
| 5,891,082 | A | 4/1999 | Leone |
| 5,928,182 | A | 7/1999 | Kraus |
| 5,957,912 | A | 9/1999 | Heitzmann |
| 6,503,507 | B1 | 1/2003 | Allen |
| 6,527,759 | B1 | 3/2003 | Tachibana |
| 6,572,586 | B1 | 6/2003 | Wojcik |
| 6,592,888 | B1 | 7/2003 | Jensen |
| 6,602,274 | B1 | 8/2003 | Chen |
| 6,605,751 | B1 | 8/2003 | Gibbins |
| 6,680,277 | B2 | 1/2004 | Morikawa |
| 6,743,749 | B2 | 6/2004 | Morikawa |
| 6,866,755 | B2 | 3/2005 | Monzyk |
| 6,991,768 | B2 | 1/2006 | Keras |
| 7,211,513 | B2 | 5/2007 | Remington, Jr. |
| 7,582,068 | B2 | 9/2009 | Koullick |
| 2003/0125679 | A1* | 7/2003 | Kubota et al. ............ 604/265 |
| 2003/0204229 | A1 | 10/2003 | Stokes |
| 2004/0030278 | A1 | 2/2004 | Cowan |
| 2004/0254522 | A1 | 12/2004 | Kraus |
| 2005/0175658 | A1 | 8/2005 | DiMauro |

FOREIGN PATENT DOCUMENTS

| | | |
|---|---|---|
| JP | 2002113108 | 4/2002 |
| JP | 2003260126 | 9/2003 |

OTHER PUBLICATIONS

Anpo, "Utilization of TiO2 photocatalysts in green chemistry", Pure Appl. Chem., 2000, pp. 1265-1270, vol. 72(7).

Kaplan, "Biomaterial-induced alterations of neutrophil superoxide production", J. Biomed. Mat. Res., 1992, pp. 1039-1051, vol. 26.

Ohko, "Self-sterilizing and self-cleaning of silicone catheters coated with TiO2 photocatalyst thin films—A preclinical work", J. Bio. Med. Mat. Res., 2001, pp. 97-101 vol. 58.

Ramires, "The influence of titania/hydroxyapatite composite coatings on in vitro osteoblasts behavior", Biomaterials, Jun. 2001, pp. 1467-1474, vol. 22(12).

Shah, "Study of $Nd^{3+}$, $Pd^{2+}$, $Pt^{4+}$ and $Fe^{3+}$ dopant effect on photoreactivity of TiO2 nanoparticles", PNAS, Apr. 30, 2002, pp. 6482-6486, vol. 99(S2).

Shanbhag, "Decreased neutrophil respiratory burst on exposure to cobalt-chrome alloy and polystyrene in vitro", J Biomed Mar. Res, 1992, pp. 185-195, vol. 26.

Stutzman, "GaN-based heterostructures for sensor applications", Diamond and Related Materials, 2002, pp. 886-891, vol. 11.

Trampuz, "Molecular and antibiofilm approaches to prosthetic joint infection", Clin Orthop., 2003, pp. 69-88. vol. 414.

Trepanier, "Effect of modification of oxide layer on NiTi stent corrosion resistance", J. Biomed. Mat. Res., 1998, pp. 433-440, vol. 43.

Wainright, "Photodynamic antimicrobial chemotherapy PACT", J Antimicrobial Chemotherapy, 1998, pp. 13-28, vol. 42.

Wolfrum, "Photocatalytic oxidation of bacteria, bacterial and fungal spores, and model biofilm components to carbon dioxide on titaniu, dioxide-coated surfaces", ES&T, 2002, pp. 3412-3419, vol. 36.

Yin, "Preparation of nitrogen-dopes titania with high visible light induced photocatalytic activity by mechanochemical reaction of titania and hexamethylenetetramine", Mater. Chem., 2003, pp. 2996-3001, vol. 31(12).

Zeina, "Killing of cutaneous microbial species by photodynamic therapy", Br. J. Dermatol., 2001, pp. 274-278, vol. 144(2).

Zeina, "Cytotoxic effects of antimicrobial photodynamic therapy on keratinocytes in vitro", B. J. Dermatol. 2002, pp. 568-573, vol. 146.

* cited by examiner

PHOTOCATALYTIC IMPLANT HAVING A SENSOR

CONTINUING DATA

This patent application is a continuation-in-part of co-pending U.S. Ser. No. 10/774,105, filed Feb. 6, 2004, entitled "Implant having a Photocatalytic Unit" (DiMauro et al).

BACKGROUND OF THE INVENTION

1. Field of the Invention

This invention relates to a prosthetic implant having a photocatalytic layer adapted to fight periprosthetic infection.

2. Description of the Related Art

It is well known that infections occur in about 1% to about 5% of all primary arthroplasties, and that "the economic impact, the morbidity, and the emotional trauma of prosthetic joint infection is immense and devastating to the patient and society". Trampuz et al., Clin. Orthop., (414), 2003 pp. 69-88. It is believed that a majority of these infections occur via transmission from microbes upon the surgical gloves, the patient's skin, implants or instruments. Unlike routine systemic infections, infections associated with implants ("periprosthetic infections") are particularly troublesome.

It has been reported that certain biomaterials cause an abnormal and inferior immune response. In short, a portion of the immune response is provided by the release of superoxide ions, such as hydroxyl radicals, that are lethal to microbes. However, when a periprosthetic infection occurs, it has been reported that biomaterials such as cobalt chrome alloys cause abnormal neutrophil activity, resulting in an inferior non-productive immune response. Shanbhag, *J. Biomed. Mar. Res.*, Vol. 26, 185-95, 1992.

It appears that the presence of the implant surface helps the microbes survive both the immune response and antibiotic treatment. In particular, microbes of concern attach to the implant surface and form a polymer-like glaze (or "biofilm") between themselves and the local environment. This biofilm acts as an effective barrier to both neutrophils and antibiotics.

Although the periprosthetic infection itself is a primary concern for the patient, it is also known that the immune response triggered by the body to fight the infection also results in bone loss. In particular, the increased phagocyte concentration also increases the local concentration of tumor necrosis factor (TNF-α). The TNF-α concentration in turn upregulates the local level of osteoclasts. These increased osteoclast concentration uncouples the normal balance in bone metabolism, thereby leading to localized bone loss. This localized bone loss may result in the loosening of the implant, thereby necessitating its removal.

U.S. Pat. No. 6,503,507 ("Allen") discloses the use of a light-activated composition that produces singlet oxygen. Allen discloses that the singlet oxygen produced therefrom is effective in killing bacteria. U.S. Pat. No. 6,527,759 ("Tachibana") discloses the use of light activated drugs that produce singlet oxygen.

Implant Sciences Corp. has promoted a surface treatment for percutaneous medical devices that prevents the growth of bacteria by employing the germ-fighting properties of silver coatings. U.S. Pat. No. 6,592,888 ("Jensen") discloses the use of metallic compounds in wound dressings to produce antimicrobial effects. U.S. Pat. No. 6,605,751 ("Gibbins") discloses the use of silver containing anti-microbial hydrophilic compositions. US Patent Application 20030204229A1 ("Stokes") discloses the use of a polymeric casing containing cations as biologically active agents to be used on medical implants and devices.

Ohko, *J. Biomed. Mat. Res. (Appl Biomat)* 58: 97-101, 2001 reports coating titania upon silicone catheters and medical tubes, and illuminating those tubes with UV light. Ohko further reported the bactericidal effect of the subsequent photocatalysis on *E. coli* cells. However, Ohko states that $TiO_2$ is toxic under illumination, and that because the part of the $TiO_2$ coating buried in the patient's body can not be illuminated, the coating should not be harmful to the body. Therefore, it appears that Ohko discourages the in vivo irradiation of titania.

US Published Patent Application 2003/0125679 ("Kubota") discloses a medical tube comprising an elastomer and a photocatalyst layer, wherein the tube has excellent antibacterial activity.

Trepanier, *J. Biomed. Mat. Res. (Appl Biomat)* 43, 433-440 (1998) reports providing an oxide layer of less than 1000 angstroms upon a NiTi cardiovascular stent.

SUMMARY OF THE INVENTION

According to some embodiments of the invention, an implant comprises a surface adapted for attachment to bone, with the surface comprising a semiconductor oxide. According to some embodiments of the invention, the semiconductor oxide has an average pore size of no more than 10 um and a thickness of at least 0.2 um.

According to some embodiments of the invention, an implant comprises a base material having an outer surface, a wave guide, and a photocatalytic layer. The wave guide comprises an inner surface and an outer surface, wherein the inner surface of the wave guide is disposed adjacent the outer surface of the base material. The photocatalytic layer comprises a semiconductor oxide having an inner surface disposed adjacent the outer surface of the wave guide.

According to some embodiments of the invention, an implant comprises a base material having an outer surface, a waveguide and a light port. The wave guide comprises an inner surface disposed adjacent the outer surface of the base material and the light is port coupled to the waveguide and adapted to receiving a light signal.

According to some embodiments of the invention, an implant comprises a photocatalytic layer comprising a semiconductor oxide having an outer surface that is doped.

According to some embodiments of the invention, an implant comprising a semiconductor oxide having an outer surface that has a maximum light absorption wavelength of at least 400 nm.

According to some embodiments of the invention, an implant comprises a base material having an outer surface, a semiconductor oxide layer and a reflective material. The semiconductor oxide comprises an inner surface and an outer surface, wherein the inner surface of the semiconductor oxide is disposed adjacent the outer surface of the base material, and the reflective material has inner surface that is disposed upon the outer surface of the semiconductor oxide.

According to some embodiments of the invention, an implant comprises a composite material comprising a first material and a second material. The first material has a transmissivity of at least 50% when exposed to a predetermined wavelength of light; and the second material has photocatalytic activity when exposed to the predetermined wavelength of light.

According to some embodiments of the invention, a biomedical implant comprises a photocatalytic surface and a light source adapted to irradiate the photocatalytic surface. The light source and the photocatalytic surface are configured such that the irradiation of the photocatalytic surface with the light source produces a photocatalytic effect.

According to some embodiments of the invention, a photocatalytic system comprises an implant having a photocatalytic surface and an external light source adapted to irradiate the photocatalytic surface of the implant.

According to some embodiments of the invention, a method of treating a prosthetic implant, comprising the acts of implanting an implant having a photocatalytic surface into a patient, and irradiating the photocatalytic surface to produce a photocatalytic effect within the patient.

According to some embodiments of the invention, a prosthetic vertebral endplate comprises a first surface, a second surface, a body portion and an oxide surface. The first surface is adapted to mate with a vertebral body. The second surface comprises an articulation surface suitable for supporting articulation motion. The body portion connects the first and second surfaces, and the oxide surface is a titanium dioxide ($TiO_2$) surface.

According to some embodiments of the invention, a prosthetic vertebral endplate comprises a first surface, a second surface and a functional unit. The first surface is adapted to mate with a vertebral body. The second surface comprises a substantially central articulation surface suitable for supporting articulation motion, with the articulation surface defining first and second lateral portions of the vertebral endplate. The functional unit can be located adjacent one of the first and second lateral portions of the endplate.

According to some embodiments of the invention, a method of performing a procedure upon a patient, comprising the acts of providing a cylinder comprising an outer surface having a photocatalytic layer, advancing the cylinder through a tissue of the patient, and, irradiating the photocatalytic layer of the cylinder so that at least a portion of the irradiated photocatalytic layer is in contact with the tissue.

According to some embodiments of the invention, a cylinder for penetrating a tissue of a patient, comprises a distal end portion adapted to penetrate tissue, an elongated intermediate portion, a proximal portion, a base material forming an outer surface; and a photocatalytic layer disposed upon at least a portion of the outer surface.

According to some embodiments of the invention, a sterilization system comprises a cylinder for penetrating a tissue of a patient and a light transmission device coupled to the proximal end portion of the cylinder. The cylinder comprises a distal end portion adapted to penetrate tissue, an elongated intermediate portion, a proximal portion, a base material forming an outer surface, and a photocatalytic layer disposed upon at least a portion of the outer surface of the base material.

According to some embodiments of the invention, a method of disinfecting skin of a patient, comprises the acts of providing a substrate comprising a photocatalytic layer, contacting the photocatalytic layer with a liquid comprising oxygen, irradiating the photocatalytic layer of the substrate in contact with the liquid to produce reactive oxygen species, and contacting the reactive oxygen species with the skin of the patient.

According to some embodiments of the invention, a shunt device comprises a structural component housed within a tubing. The tubing comprises an outer tube having an outer wall and an inner wall, a photocatalytic layer attached to the inner wall of the outer tube, and a light port.

According to some embodiments of the invention, a shunt device comprises a structural component housed within a tubing. The structural component comprises a baseplate having a first surface, and a photocatalytic layer disposed upon a first portion of the first surface of the baseplate.

According to some embodiments of the invention, a method of performing a procedure upon a patient comprises the acts of providing a shunt comprising a structural component housed within a tubing having an inner surface, wherein at least one of the structural component and the inner surface of the tubing has a photocatalytic layer disposed thereon, implanting the shunt in the patient, and irradiating the photocatalytic layer.

According to some embodiments of the invention, an infusion set comprises a needle housing, a mounting pad, and a transcutaneous cannula. The needle housing has a proximal port, a distal port and a base surface. The mounting pad is coupled to the base surface of the needle housing. The transcutaneous cannula has a proximal end connected to the distal port of the needle housing and a distal end. The transcutaneous cannula also has an ex vivo portion and an in-dwelling portion, and comprises an inner silicon tube having an outer wall and an inner wall, and an outer photocatalytic layer attached to the outer wall of the silicon tube.

DESCRIPTION OF THE DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE INVENTION

Figure 1:
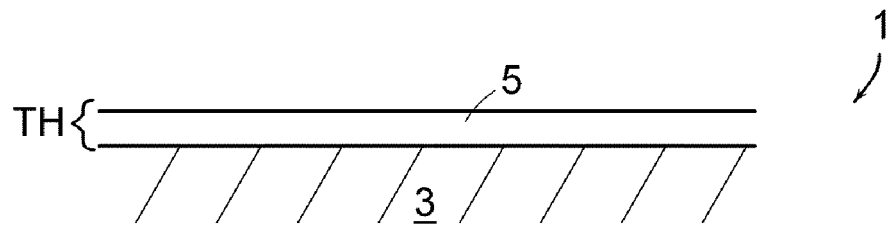
FIG. 1 is a cross-section of a surface portion of a titanium implant, wherein the surface has been oxidized to produce a thick titania layer.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

For the purposes of the present invention, "titanium dioxide" is also referred to as titania and $TiO_2$. A "UV light source" includes any light source emitting light having a maximum energy wavelength of between about 0.1 nm and about 380 nm. A "UVC light source" includes any light source emitting light having a maximum energy wavelength of between about 0.1 nm and less than 290 nm. A "UVB light source" includes any light source emitting light having a maximum energy wavelength of between 290 nm and less than 320 nm. A "UVA light source" includes any light source emitting light having a maximum energy wavelength of between 320 nm and less than 380 nm. A "visible light source" includes any light source emitting light having a maximum energy wavelength of between 380 nm and less than 780 nm. An "infrared light source" includes any light source emitting light having a maximum energy wavelength of between 780 nm and less than one million nm.

A "reactive oxygen species" includes, for example, hydrogen peroxide, hydroxyl radicals, superoxide ion, and singlet oxygen and is also referred to as "ROS".

As will be discussed in detail infra, one aspect of the invention comprises a photocatalytic unit (PCO) comprising a photocatalytic layer. For example, some embodiments of the photocatalytic unit comprise an implant device having a photocatalytic layer. The PCO may also comprise a light source. Upon illumination of the photocatalytic layer with light from the light source, the photocatalytic layer locally generates a plurality of reactive oxygen species, such as singlet oxygen. The reactive oxygen species (ROS) produced by this system are potent anti-microbial agents capable of destroying not only local microbes but also periprosthetic biofilms. However, because of the potency of the ROS, the ROS typically react very quickly with surrounding organic material and so have a very local effect.

According to some embodiments, the photocatalytic layer comprises a semiconductor material, and is can be a metal oxide, such as titanium dioxide. Titanium dioxide has been shown to have photocatalytic activity for generating ROS.

In some embodiments, the implant device is illuminated with an external source of light. For example, the light source could be the operating room lights. The light source could also be an external light box in which the device is placed just prior to implantation. In other embodiments, a suitable fiber-optic device is connected to the external light source and passed through the patient's skin to connect with the implanted device.

In some embodiments, the photocatalytic layer of the implant device is doped to enhance or prolong the photocatalytic effect. Some exemplary dopants include, but are not limited to, metal alloys or ions of chromium and/or vanadium; phosphorescent compounds, ligands, or ions; organic compounds containing oxygen-rich chemical species such as peroxides, superoxides, acids, esters, ketones, aldehydes, ethers, epoxides, and lactones; and organic compounds containing conjugated systems, such as photostabilizers and dyes.

Alternatively or additionally according to some embodiments, the implant device could be illuminated after implantation and all surgical manipulations have been performed. Such post-implantation illumination could be performed just prior to surgical closure, for example, or after some period of time has elapsed by a percutaneous access approach using a fiber-optic surgical delivery device.

In some embodiments, a light port is incorporated into the implant device to provide efficient delivery and coupling of the light energy to the photocatalytic layer. The light port can include a self-sealing gland to prevent contamination and occlusion of the light receiving port, thereby providing efficient energy transfer. Additionally, the light port could include a radiopaque marker, e.g. a tapered cylinder or other geometry, to allow the surgeon to efficiently direct a percutaneous needle with a fiber optic to the desired site under fluoroscopic guidance.

According to some embodiments, the implant device could comprise a waveguide layer to deliver light energy to the photocatalytic layer. The waveguide layer could, for example, be located underneath the photocatalytic layer, e.g. between the photocatalytic layer and the base material of the implant. It may be desirable for the waveguide layer to be of a different material than the photocatalytic layer to allow efficient energy transfer. For example, an undoped titanium oxide layer uses light having a wavelength of less than 380 nm to induce the photocatalytic effect. However, titanium oxide is moderately to strongly light absorbing at wavelengths below ~450 nm, and so would not function efficiently as a waveguide to propagate the light to all areas of the implant device. Accordingly, the use of a UV transmissive material as the waveguide layer, such as silicon oxide, aluminum oxide, or other materials with low absorption at the relevant wavelengths, would allow the light to reach regions distant from the light port or entry point.

According to some embodiments of an implant device, there can be provided a partially reflecting layer on at least one surface of the waveguide layer that would enhance the transmission of light energy within the waveguide. For example, it may be desirable to have the surface adjacent to the photocatalytic layer be partially reflective or transmissive, with all other surfaces of the waveguide totally reflective. In some embodiments, silver metal is used as the reflective layer, having known desirable optically reflective properties as well as known anti-microbial properties. It is to be appreciated that alternative reflective materials such as aluminum or gold metal can also be used.

According to some embodiments, dopants as described above, and particularly metal ions, are provide to the photocatalytic layer which comprises titanium oxide so as to modify the band gap energy of the titanium oxide layer, such that visible light greater than 380 nm can be used to effectively induce the photocatalytic activity. For such embodiments, the photocatalytic layer could also act as the waveguide layer, and a partially reflective silver coating could be provided to enhance the internal reflection of the light to efficiently spread the light energy throughout the layer. As discussed herein, the selection of silver for the reflective layer also provides additional anti-microbial activity.

In some embodiments involving, for example, orthopedic implants, the implant can incorporate a porous layer on surfaces in direct contact with bone to facilitate osseointegration. These porous layers can be fabricated, for example, from titanium using a plasma-spray method, generating pore sizes ranging from 10 μm to ~500 μm, with ~200-300 μm being an exemplary useful range. According to some embodiments, the porous network can also deliver therapeutic fluids, e.g. antibiotics, hormones, growth factors, BMP's, anti-inflammatory agents, etc. Since titanium readily forms an oxide on its surface, this porous layer may be utilized as a waveguide and photocatalytic layer, as well as a fluid channel to deliver therapeutic fluids to the surfaces of the device. For example, the delivery of fluid to this layer may be achieved by the use of the light port as described above, and using a standard hypodermic needle (e.g., without a fiber optic), to deliver fluid to the light port instead of or in addition to light.

According to some embodiments, a coating or layer of resorbable material can be provided on the surface of the device to partially or completely seal the surface to enhance the delivery of fluid throughout the device, thus preventing delivered fluid from immediately leaking out of the delivery site and not spreading uniformly throughout the porous layer. Such a coating or layer may be made of silver metal, thereby generating the desirable properties of anti-microbial activity and also reflectivity for the waveguide/photocatalytic aspects of the layer.

According to one aspect of the invention, it is believed that the photocatalytic unit of the present invention works to effectively fight a periprosthetic infection (PPI) as is disclosed herein.

It is known that neutrophils play a critical role in fighting infection in the body. It is believed that when the body recognizes a foreign body, such as an implant, signaling from the immune system calls neutrophils to the implant location. The neutrophils proceed to emit a number of infection-fighting molecules, including reactive oxygen species (ROS), such as superoxide ion. It is believed that the ROS, and the superoxide ion in particular, cause the death of the pathogenic bacteria by penetrating the cells wall of the bacteria.

Kaplan et al., *J. Biomed. Mat. Res.*, 26, 1039-51 (1992) investigated the role played by neutrophils in periprosthetic infection (PPI) and found that the neutrophils prematurely emit their infection-fighting compounds and, when the infection is sustained, appear to exhaust their capability of manufacturing more of these infection fighting compounds. Accordingly, it appears that the body response to PPI includes a dose of apparently potent compounds, but that dose is not sustained. When the release period ends, the body does not adequately respond to the PPI.

In sum, the typical immune response of the body to an infection involves the release of superoxide ions by local neutrophils in amounts that are lethal to the local bacteria, and periprosthetic infection often arises due to the implant's interference with this natural activity.

When the semiconductor element of the PCO of the present invention is properly irradiated by the UV light source, it is believed that reactive oxygen species (ROS) are produced at the semiconductor surface and enter the body fluid adjacent the photocatalytic surface. These ROS include hydroxyl radicals (.OH), hydrogen peroxide ($H_2O_2$), superoxide ion ($^-O_2$) and singlet oxygen (O) and appear to be the same ROS naturally produced by neutrophils in the natural immune response to PPI. However, whereas the neutrophil response is limited both in magnitude and duration, the PCO unit of the present invention can be tuned to emit ROS in both a magnitude and for a duration deemed appropriate for the extent of infection diagnosed by the clinician.

According to some embodiments, when an effective amount of light irradiates the photocatalytic surface of the PCO of the present invention, the sensitized surface can effectively catalyze both the oxidation of water (to produce hydroxyl radicals .OH) and the reduction of oxygen (to produce superoxide radicals $^-O_2$). It is believed that PCO may also produce significant amounts of hydrogen peroxide.

Accordingly, activation of the PCO unit disposed on an implant can effectively produce and release the same molecular units naturally released by the patient's full-strength immune system. Therefore, it is believed that at least the superoxide radicals $O_2$— produced by the PCO unit effectively kill at least the free floating bacteria that are not protected by a biofilm.

As stated above, it is believed that the PCO unit of some embodiments of the present invention comprising a semiconductor device, causes the production of hydrogen peroxide near or upon the semiconductor surface. It is well known that hydrogen peroxide is lethal to bacteria. In some embodiments, the PCO unit produces a local concentration of hydrogen peroxide believed to be sufficient to kill *Staphylococcus epidermis*. In some embodiments, the PCO unit can be constructed and arranged to produce a local concentration of hydrogen peroxide in the range typically produced by natural neutrophils in response to an infection. In some embodiments, the PCO unit can be constructed and arranged to produce a local concentration of hydrogen peroxide believed to be sufficient to oxidize a biofilm.

As stated above, the PCO unit of the present invention comprising a semiconductor device can be constructed and arranged to cause the production of superoxide ion upon the semiconductor surface. It is well known that superoxide ion is lethal to bacteria. In some embodiments, the PCO unit can be constructed and arranged to produce a local concentration of superoxide ion believed to be sufficient to kill *Staphylococcus epidermis*. In some embodiments, the PCO unit can be constructed and arranged to produce a local concentration of superoxide ion in the range typically produced by natural neutrophils in response to an infection. In some embodiments, the PCO unit can be constructed and arranged to produce a local concentration of superoxide ion believed to be sufficient to oxidize a biofilm.

As stated above, the PCO unit of some embodiments of the present invention comprising a semiconductor device can be constructed and arranged to cause the production of hydroxyl radicals upon the semiconductor surface. It is well known that hydroxyl radicals are particularly lethal to bacteria. In some embodiments, the PCO unit can be constructed and arranged to produce a local concentration of hydroxyl radicals believed to be sufficient to kill *Staphylococcus epidermis*. In some embodiments, the PCO unit can be constructed and arranged to produce a local concentration of hydroxyl radicals in the range typically produced by natural neutrophils in response to an infection. In some embodiments, the PCO unit can be constructed and arranged to produce a local concentration of hydroxyl radicals believed to be sufficient to oxidize a biofilm.

As stated above, it is believed that the PCO unit of some embodiments of the present invention comprising a semiconductor device, can be constructed and arranged to cause the production of hydrogen peroxide upon the semiconductor surface. It is believed that providing some embodiments of the PCO upon an implant surface will produce singlet oxygen ($^1O_2$) through the following mechanism:

According to Allen, in the presence of sufficient halide, $H_2O_2$ is the rate limiting substrate for haloperoxidase microbicidal action. Microbicidal activity is linked to haloperoxidase generation of hypohalous acid:

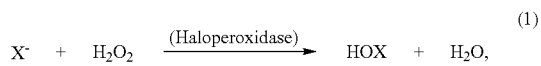

(1)

and to the secondary generation of singlet molecular oxygen ($^1O_2$):

(2).

Both HOX and $^1O_2$ are antimicrobial reactants.

The present inventors have appreciated that the PCO can be constructed and arranged to produce both superoxide ion and hydrogen peroxide, and that typical human interstitial fluid contains a substantial amount of salts and so has significant amounts of Cl⁻, a halide ion. Therefore, it is reasonable to conclude that the native halide ion present in the vicinity of the implant and the PCO-generated hydrogen peroxide may react to produce HOX, and this HOX will further react with another $H_2O_2$ molecule to produce singlet oxygen.

It is well known that singlet oxygen is lethal to bacteria. In some embodiments, the PCO unit can be constructed and arranged to produce a local concentration of singlet oxygen believed to be sufficient to kill free-floating microbes. In some embodiments, the PCO unit can be constructed and arranged to produce a local concentration of singlet oxygen in the range typically produced by natural neutrophils in response to an infection. In some embodiments, the PCO unit can be constructed and arranged to produce a local concentration of singlet oxygen believed to be sufficient to oxidize a biofilm.

Although it appears that singlet oxygen is a very potent antibiotic, its extreme reactivity limits its sphere of influence. In particular, it is believed that singlet oxygen has an average lifetime on the order of milliseconds and a sphere of influence of only about 0.2 microns. Therefore, the production of singlet oxygen provides a comprehensive disinfecting response, but only very close to the surface of the implant so that the nearby tissue is essentially unaffected.

Moreover, the present inventors have further appreciated the role played by chain reactions in ROS chemistry, and the need to insure that such reactions are self-limiting. It is believed that, since the production of singlet oxygen requires two hydrogen peroxide molecules, the above-stated reactions can be well-controlled due to the eventual depletion of hydrogen peroxide.

In addition, it has been recently reported by Wolfrum, *ES& T*, 2002, 36, 3412-19 that photocatalytic oxidation effectively destroys biofilms. Wolfrum reported that the reactive oxygen species produced by its PCO unit effectively oxidized each of a phospholipid, a protein and a polysaccharide film. Since Wolfrum further stated that these substance were selected to be models of polymer-like biofilm, it is reasonable to conclude that such a PCO can not only destroy the biofilm protecting the foreign microbes, but in doing so it will expose the previously protected bacteria to lethal amounts of both hydroxyl radicals (.OH) and superoxide radicals $O_2$—.

Some embodiments of the photocatalytic unit of the present invention comprise a light source and a photocatalytic surface comprising a semiconductor material to be irradiated by the light source. It is believed that, upon irradiation with an effective amount of UV light, the semiconductor material can be provided in an amount sufficient in the photocatalytic surface to produce a sufficient amount of holes and electrons. The holes catalyze the oxidation of water, thereby producing hydroxyl radicals .OH. The electrons catalyze the reduction of oxygen, thereby producing superoxide radicals $O_2$—.

Accordingly, the semiconductor material according to some embodiments comprises a solid catalyst comprising a transition element, and according to some embodiments is selected from the group consisting of titanium dioxide and ferric oxide. According to some embodiments, it comprises titanium dioxide. In some embodiments, the semiconductor is Degussa P25, available from DeGussa.

In some embodiments, the photocatalytic surface is produced by layering (for example by sonication) a powder comprising the semiconductor material upon a surface capable of being irradiated by the light source.

Now referring to FIG. 1, in some embodiments, there is provided an implant 1 of the present invention, wherein a photocatalytic layer 5 is produced by oxidizing a base material 3 comprising titanium, thereby producing a photocatalytic titania layer. According to some embodiments, the photocatalytic titania layer has a thickness TH of at least 0.2 um. Since many implants are made of titanium or titanium alloys, the photocatalytic surface may be easily produced by simply oxidizing a titanium surface on a portion of a titanium-containing implant. According to some embodiments, the oxidized surface resides in a non-load bearing portion of the implant.

In some embodiments, since titania at least partially transmits UV light, the thickness of the oxidized layer may be selected to be sufficiently thick so as to also act as a waveguide. Therefore, in some embodiments, the photocatalytic surface has a thickness of between about 0.5 um and about 1.5 um, and preferably between about 0.8 and 1.2 um.

In some embodiments, the photocatalytic surface is produced by providing sintered $TiO_2$ beads upon an implant surface. In some embodiments to be discussed infra, the $TiO_2$ beads can be sintered onto an implant-bone interface to create a porous scaffold suitable for bony in-growth. For such arrangements, the porous scaffold comprising the semiconductor oxide provides desirable qualities including disinfection capabilities (due to its photocatalytic qualities) and bone ingrowth capabilities (due to its porous scaffold).

Moreover, the porous scaffold of this embodiment can be configured to provide a convenient reaction zone for the photocatalytic process. The PCO unit can therefore be tuned to provide ROS throughout the reaction zone, while avoiding the diffusion of ROS outside the reaction zone.

Since photocatalysis is a surface phenomenon, the depth of the photocatalytic surface need not be particularly great. Moreover, it has been reported by Ohko, J. Biomed. Mat. Res. (Appl Biomat) 58: 97-101, 2001 that when $TiO_2$ thin films produced by heat treating exceed about 2 um, the layer begins to peel from its substrate. Therefore, in some embodiments, the photocatalytic surface has a thickness of between about 0.2 um and about 2 um. However, it is to be appreciated that the thickness can be outside of this range, for example, as discussed above, in some embodiments, the thickness of the photocatalytic layer may be configured so as to act as a waveguide.

According to some embodiments, the photocatalytic surface comprises a semiconductor material. According to some embodiments, the semiconductor material is selected from the transition elements of the Periodic Table. According to some embodiments, the semiconductor material is selected from the group consisting of titanium dioxide and ferric oxide. According to some embodiments, the semiconductor is titania. In some embodiments, the semiconductor is Degussa P25.

In some embodiments, the photocatalytic surface consists essentially of the semiconductor material. These embodiments have the advantage of manufacturing simplicity. In other embodiments, the photocatalytic surface can comprise a composite comprising at least a semiconductor material. According to some embodiments, the photocatalytic surface can comprise a titania film on a titanium surface. For example, Akin, *J. Biomed. Mat. Res.* 57, 588-596, 2001, discloses the preparation of macroporous titania films upon titanium surfaces Akin's films were reported to be about 0.1 mm to about 1 mm in thickness. Pore sizes were reported to be 0.5 um, 16 um and 50 um.

In some embodiments, the photocatalytic surface comprises a composite of a semiconductor material and a material suitable for providing a scaffold for bony ingrowth. In some embodiments, the scaffold material comprises a calcium phosphate (CaP) containing material. According to some embodiments, the CaP-containing material is selected from the group consisting of tricalcium phosphate (TCP) and hydroxapatite (HA). The literature has reported that films comprising $HA/TiO_2$ are highly suitable for the formation of a porous scaffold suitable for bony ingrowth. See, e.g., Ramires, *Biomaterials* 2001, June; 22(12); 1467-74.

In some embodiments, the photocatalytic surface comprises a composite of a semiconductor material and a light-transmissible material. According to some embodiments, the light transmissible material is a UV-transmissible material. According to some embodiments, the UV-transmissible material is selected from the group consisting of alumina, sapphire and silica. Moreover, according to some embodiments this composite is made into a porous scaffold, wherein the porous scaffold contains islands of $TiO_2$ interspersed throughout the porous scaffold. Because the UV light is not absorbed by the UV-transmissible portion of the material, the UV light is absorbed only by the titania interspersed throughout the scaffold. The titania present adjacent an internal scaffold surface then becomes photoactivated and produces ROS throughout the scaffold.

Figure 2:
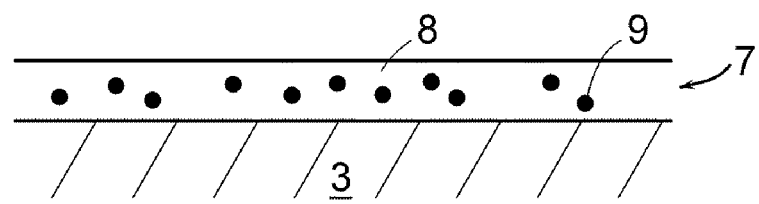
FIG. 2 is a cross-section of a surface portion of a titanium implant having an oxidized surface, wherein the surface has been further bombarded with a dopant.

Now referring to FIG. 2, in some embodiments, the implant comprises a base material 3 overlain by a photocatalytic layer 7. In this case, the photocatalytic layer 7 comprises a composite layer of a semiconductor material 8 doped with a dopant 9 that reduces the bandgap of the photocatalyst, thereby increasing the maximum wavelength of light absorbed by the photocatalytic layer. In some embodiments, the dopant is selected from the group consisting of vanadium and chromium.

It has been reported by Anpo et al, *Pure Appl. Chem.* Vol. 72, (7), 2000, pp. 1265-70 that when a dopant selected from this group is ion-implanted onto a titanium dioxide surface, the resulting surface is substantially photocatalytically active when irradiated with white light.

In some other embodiments, the dopant is nitrogen. It has been reported by Lin, J. Mater. Chem., 2003, 13(12)2996-3001 that when nitrogen is selected as the dopant, the resulting surface is substantially photocatalytically active when irradiated with light having either a 400 nm or a 550 nm wavelength.

In some other embodiments, the dopant is selected from the group consisting of $Nd^{+3}$, $Pd^{+2}$, $Pt^{+4}$ and $Fe^{+3}$. It has been reported by Shah, PNAS, Ap. 30, 2002, 99(S.2), pp. 6482-6 that when one of these dopants is selected as the dopant, the resulting surface may be substantially photocatalytically active when irradiated with 450-460 nm light. Therefore, in some embodiments, the photocatalytic surface comprises a composite of a semiconductor material doped with a dopant that reduces the bandgap of the photocatalyst, thereby increasing the median wavelength of light absorbed by the photocatalytic layer to include wavelengths greater than UV.

In some embodiments using a dopant, a titanium implant is oxidized to produce a titania surface layer, and this titania layer is then ion-bombarded with a dopant.

It is well known that there are many commercial Ti-based alloys commonly used in the medical devices that contain vanadium. One common example of such as alloy is Ti4Al6V alloy, which comprises 90 wt % titanium, about 4 wt % aluminum, and about 6 wt % vanadium (TMD: check) [**INFO]. The present inventors believe that simple oxidation of this commercial alloy results in a photocatalytic layer comprising titania and vanadium. As noted above, this photocatalytic layer has special utility in that it can be activated by white light.

Figure 3:
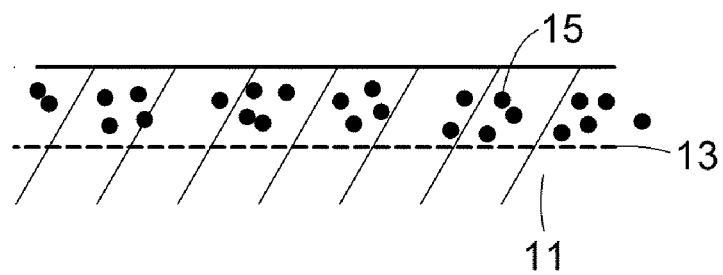
FIG. 3 is a cross-section of titanium alloy (Ti4Al6V) surface of an implant, wherein the surface has been further oxidized.

Now referring to FIG. 3, there is provided an implant having a Ti4Al6V alloy base material 11 and an oxidized surface 13. The oxidized surface is a photocatalytic layer comprising titania and vanadium 15. In some embodiments, the photocatalytic layer activated by white light has a thickness of at least 1 um.

Since periprosthetic infections often form a biofilm that envelops a substantial portion of the surface of the implant, it is appreciated that it would be highly desirable to photoirradiate substantially an entire surface of the implant. However, it is further appreciated that orthopedic implants often have irregularly shaped surfaces that are not conductive to direct irradiation from a single (or even multiple) point light source. Moreover, the presence of light-absorbing tissue adjacent the photocatalytic surface further complicates the comprehensive irradiation of a surface of the implant.

Figure 4:
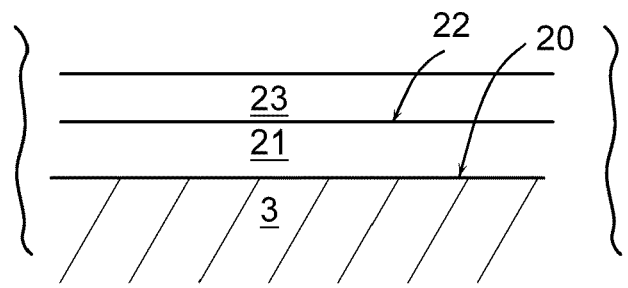
FIG. 4 is a cross-section of a portion of an implant having an intermediate waveguide layer and an upper photocatalytic layer.

Now referring to FIG. 4, accordingly, in some embodiments, the photocatalytic unit of the implant further comprises a base material 3, a photocatalytic layer 23, and an intermediate waveguide 21 adapted to transmit light from a light source to distant surface portions of the implant. According to some embodiments, the waveguide comprises a material that is at least partially transmissible to UV or white light. When such a waveguide is provided adjacent the photocatalytic layer, the light irradiating the waveguide can travel via the waveguide throughout the surface of the photocatalytic layer. One advantage is that the light transmissible material acts as a wave guide, so that the UV light generated from the light source can spread laterally across the surface of the implant and thereby irradiate the photocatalytic layer from, for example, the back side.

In some embodiments, the wave guide 21 can be provided as a discrete layer between the inner surface 22 of the photocatalytic layer 23 and the outer surface 20 of the base material 3 implant (as illustrated in FIG. 4). In such embodiments, the waveguide layer can be easily deposited by CVD processes.

Figure 5:
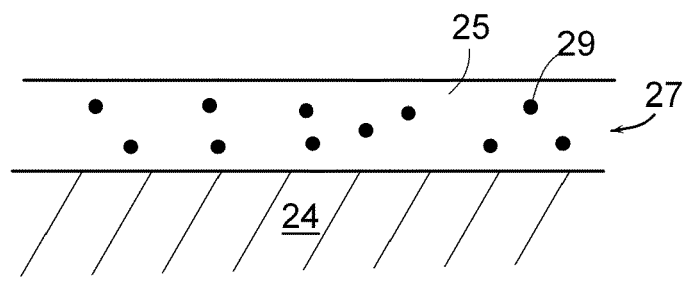
FIG. 5 is a cross-section of a portion of an implant having a composite coating comprising a waveguide and a photocatalytic material.

Now referring to FIG. 5, in other embodiments, the wave guide can be provided as part of a composite layer 27 comprising the semiconductor material 29 and a light-transmissible (for example, UV-transmissible) material 25. With this arrangement, the composite layers act as both a wave guide and a photocatalytic surface. In some embodiments, the composite layer 27 comprises between about 10 vol % and 20 vol % semiconductor and between about 80 vol % and 90 vol % waveguide. In some embodiments of the composite layer 27, the composite is essentially dense (e.g., no more than 10 vol % porous), thereby providing strength.

Figure 6:
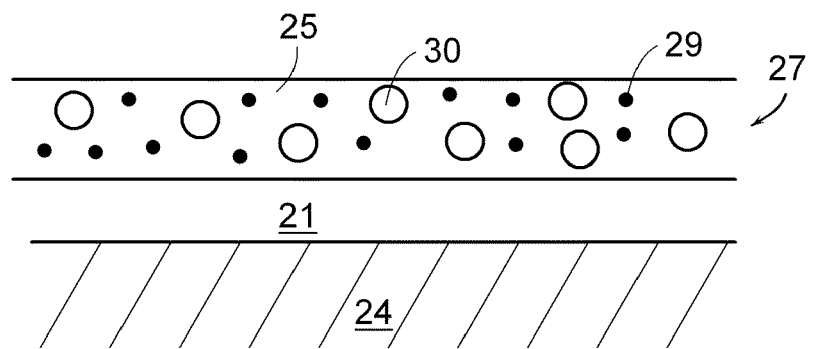
FIG. 6 is a cross-section of a portion of an implant having a porous composite coating comprising a waveguide and a photocatalytic material.

Now referring to FIG. 6, in other embodiments, the implant comprises a base material 3 having an outer surface 20, a wave guide 21 contacting the outer surface of the base material, and a composite layer 27 overlying the wave guide and comprising a UV transmissible material 25, including a semiconductor material 29 and also having an open porosity 30. In some embodiments, the composite layer has a porosity having an average pore size of between about 50 um and about 1000 um. This composite layer (e.g., alumina-titania) can also act as a porous scaffold over the entire surface, thereby providing an osteoconductive surface suitable for bony ingrowth.

In some embodiments of this arrangement, the light transmissible material is selected from the group consisting of a ceramic and a polymer. In some embodiments, suitable UV-transmissible ceramics include alumina, silica, CaF, titania and single crystal-sapphire. In some embodiments, suitable light transmissible polymers can be selected from the group consisting of polypropylene and polyesters.

According to such embodiments of this arrangement, irradiation of any surface of the waveguide may be sufficient for the waveguide to propogate the light throughout the adjacent photocatalytic surface and generate ROS over that entire photocatalytic layer. Although comprehensive irradiation is easily accomplished when performed at the time of surgery (when the implant is visible to the surgeon), if anti-microbial therapy is desired at some future, post-operative time, then, for example, a minimally invasive fiber optic device may be used to deliver the light to the waveguide, where irradiation of the entire surface of the waveguide or photocatalytic surface may be more problematic.

Figure 7:
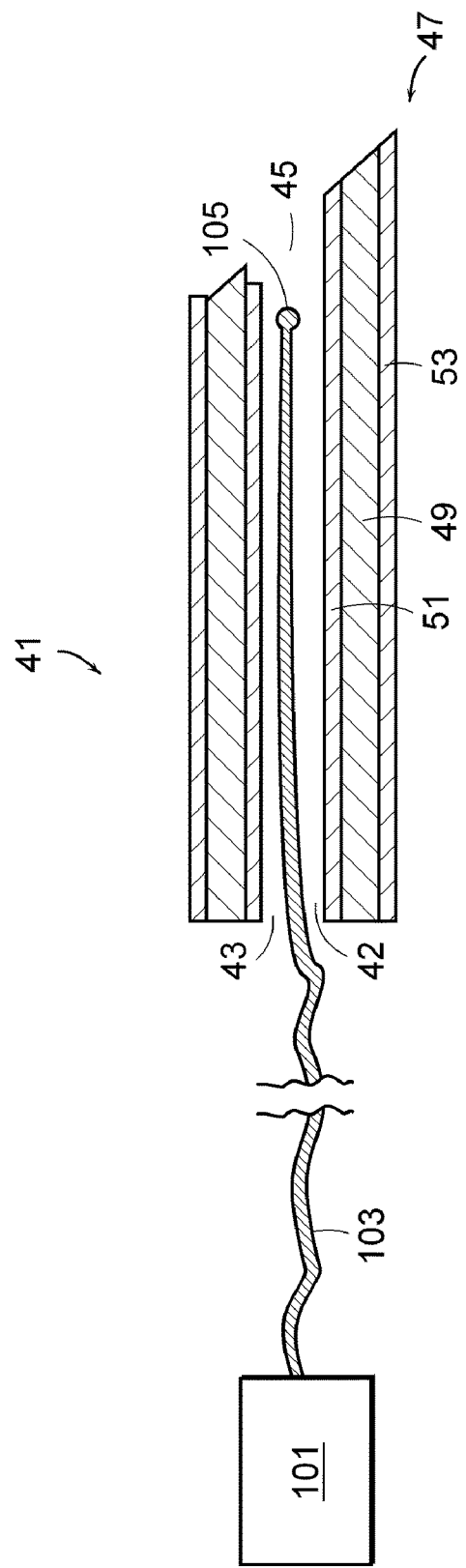
FIG. 7 is a cross section of a needle containing a fiber optic cable.
Figure 8:
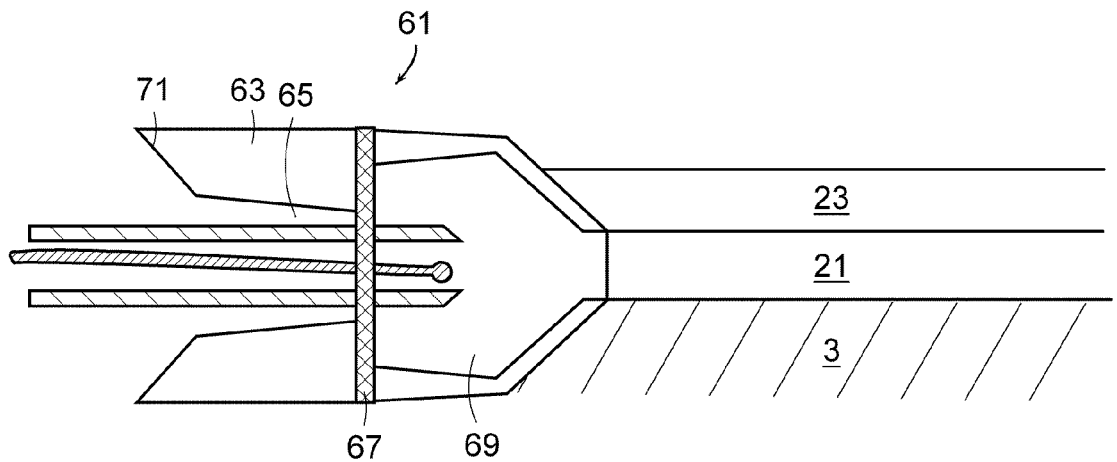
FIG. 8 is a cross section of a portion of an implant having a port for connecting a fiber optic.

Accordingly, and now referring to FIGS. 7 and 8, when a wave guide is used in conjunction with an external light source and light is to be transmitted to the wave guide via a fiber optic, it is desirable to provide a light port coupled to the wave guide in order to provide easy connection of the fiber optic to the wave guide.

FIG. 7 discloses a distal portion of a delivery needle 41 adapted to deliver a fiber optic 103 to the waveguide. The needle 41 comprises a barrel 42 defining a small bore lumen 43 and a distal opening 45. The distal portion of the barrel forms a needle tip 47 suitable for penetrating an orthogonally-disposed seal (not shown). In some embodiments, the delivery needle can also be adapted to contain both a waveguide 49 and inner 51 and outer photocatalytic surfaces 53, so that the needle itself can be photo-sterilized to minimize introduction of bacteria into or drawing bacteria from the implant site.

As shown in FIG. 7, the needle is adapted to house a fiber optic cable 103 that is connected to a light source 101. Light is generated by the light source, is transported through the fiber optic cable, and is emitted from the distal end 105 of the fiber optic cable.

Now referring to FIG. 8, there is provided an implant comprising: a base material 3, a waveguide 21 overlying the base material, a photocatalytic layer 23 overlying the waveguide, and a light port 61 communicating with the waveguide. The light port according to some embodiments comprises a proximal receiving portion 63 adapted to receive and secure the delivery needle and includes a throughbore 65, an intermediate seal 67 sealing the throughbore, and a distal barrel portion 69.

In FIG. 8, the proximal receiving portion of the light port comprises an inner bore 65 having a distally tapering circumference 71. It may also have a radio-opaque portion (not shown) that helps the surgeon find its location under fluoroscopy. The distally tapering circumference of the proximal receiving portion helps guide the needle, as illustrated and such as shown in detail in FIG. 7, into the proximal receiving portion. The proximal receiving portion may also have a securing device, such as a luer lock portion (not shown) in order to secure the needle within the light port. In some other embodiments, the securing device comprises a threaded recess adapted to mate with a threaded male distal portion of the delivery needle or fiber optic One function of the intermediate seal 67 is to prevent tissue ingress to the light-communicating surface of the optically transmissible waveguide. One function of the distal bore portion 69 is to provide a space allowing for needle over-insertion, thereby minimizing physical damage to the waveguide portion of the implant by the inserted needle. Thus, the light port of FIG. 8 receives a needle such as that of FIG. 7 to provide the light from light source 101 to the waveguide layer 21 of the implant.

Figure 9:
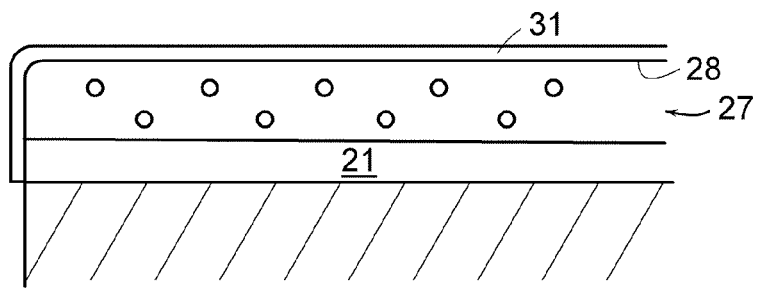
FIG. 9 is a cross-section of a portion of an implant having a waveguide layer, a photocatalytic layer, and an outer reflective layer.

However, if a wave guide is merely disposed as an interlayer between an implant surface and the photocatalytic surface, then there is a possibility that light traveling within the wave guide will simply exit the lateral ends of the wave guide and enter the adjacent tissue. In order to prevent such occurrences and thereby enhance the efficiency of the light source, in some embodiments of the present invention, and now referring to FIG. 9, the implant can be provided with a reflective surface 31 adjacent an edge of the wave guide 21, such as the distal end of the waveguide (from the end having the light receiving port). The disposition of the reflective layer at a wave guide lateral edge prevents laterally moving light from exiting the lateral edge of the wave guide, and rather reflects this light back into the wave guide and ultimately into the photocatalytic layer 27.

In other embodiments, the reflective coating 31 can also be placed on the outer surface 28 of a porous photocatalytic layer 27 in order to reflect light escaping from the photocatalytic layer and to reflect the light back into the photocatalytic layer.

In some embodiments thereof, the reflective surface comprises a metal-containing layer, for example, coated upon a portion of the waveguide or photocatalytic surface. The metal-containing layer may be for example a pure metal, a metal alloy, or even a metal oxide having a lower refractive index than the photocatalytic layer. In some embodiments, the metallic coating is selected from the group of metals consisting of silver and titanium. In some embodiments, silver is used in order to take advantage of its antimicrobial effect.

Figure 10:
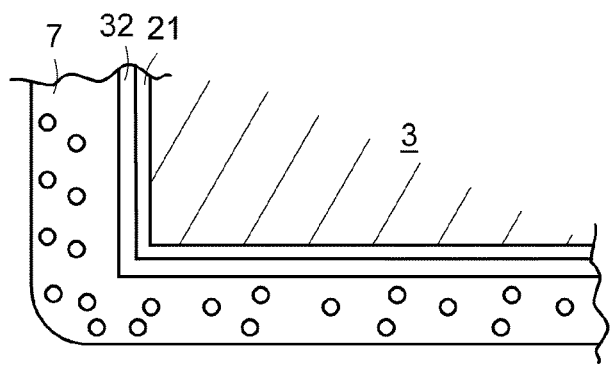
FIG. 10 is an implant having a lower waveguide layer, an intermediate reflective layer, and an outer porous photocatalytic layer.

In some embodiments, the reflective surface comprises a multi-layer structure designed to create a reflection within the waveguide layer to better distribute light to the photcatalytic layer. For example, and now referring to FIG. 10, it may be desirable to use a multi-layer structure including, for example a visible light transmissive titania as the waveguide, and an external layer of for example vanadium-doped titania as the photocatalytic surface. In particular, FIG. 10 illustrates an implant comprising base implant material 3, a wave guide layer (such as pure titania) 21 overlying the base material, a partially reflective layer 32 (such as Ti, Ag, V or Cr) overlying the waveguide layer that partially reflects the light within the waveguide to more evenly distribute the light to the photcatalytic layer, and a white light-absorbing photocatalytic outer layer 7 (for example, a vanadium-doped porous titania layer).

With such embodiments, when irradiated by white light, the waveguide layer may not generate any significant ROS (for example, the pure titania bandgap would be too high for light having a wavelength greater than 380 nm), but the external white light-absorbing layer can generate the photocatalytic effect at or near the surface of the device in response to the white light, thereby providing ROS in the region of the infection.

In some embodiments (not shown), it is desirable to create a hole or window in the reflective layer and additionally, for some embodiments, the partially reflective layer, to allow access by the fiber optic to the light port, for example at the proximal end of the waveguide of the implants discussed above, and to increase the light throughput to the waveguide. Because of this increased light throughput, a thicker, more reflective layer (e.g., 80-90% reflective) can be suitably used with more efficiency.

It is to be appreciated that other light-related components, such as bifurcated fiber optic bundles and fluorescent or phosphorescent chemical mediators, that are designed to manipulate light and allow the light to reach remote surfaces of the device can also be used to deliver light to the waveguide, and are also contemplated by the present invention.

In some embodiments, the light source is a UV light source. The UV light source is adapted to provide UV radiation to a UV-sensitive photocatalytic surface in an amount effective to produce an amount of ROS sufficient to reduce the local microbe concentration. In some embodiments, the wavelength of the UV light is UVA light and emits light having a wavelength in the range of 320 and less than 380 nm. In this range, for example, the UVA light effectively irradiates conventional $TiO_2$ and does not cause damage to DNA as does UVC light.

In some embodiments, the UV light source has a spectral maximum in the range of the UV and near-UV components of the solar spectrum. For example, the light source can be provided with a spectral maximum in the range of less than about 380 nm, and is some embodiments between 300 nm and 380 nm. In some embodiments, the light source has a spectral maximum of about 356 nm.

In some embodiments, UV or near UV light sources are used in conjunction with semiconductor materials that exhibit photocatalytic activity when irradiated by UV or near UV light. One example of a semiconductor suitably used with UV light is titania.

In other embodiments, the light source can be a white light source. The white light source can be adapted to provide white light to the photocatalytic surface in an amount effective to reduce the local microbe concentration. For example, the light source can be adapted to provide the wavelength of the white light is in the range of 380 nm-780 nm. In some embodiments, white light is used because it effectively irradiates vanadium-doped $TiO_2$ or nitrogen-doped $TiO_2$ to produce photocatalysis and does not cause damage to DNA.

In some embodiments, using doped titania as the photocatalytic surface, visible light having a maximum absorption wavelength of between 400 nm and 650 nm is used. In some embodiments, using doped titania as the photocatalytic surface, visible light having a maximum absorption wavelength of between 450 nm and 600 nm is used. In some embodiments, using doped titania as the photocatalytic surface, visible light having a maximum absorption wavelength of between 450 nm and 500 nm is used.

The present inventors have appreciated that, in some situations, it may be possible to effectively irradiate an implanted device having a photocatalytic layer, wherein the irradiation is transcutaneous. It has been reported in the literature that the effective depth of penetration of light through the skin is wavelength dependent and is approximately as follows:

| Wavelength | Depth of Penetration |
|---|---|
| 380 nm | 1 mm |
| 600 nm | 4 mm |
| 780 nm | 10 mm |

Accordingly, if the selected photocatalytic layer actives when irradiated by, for example a 600 nm wavelength light, then an implant comprising a photocatalytic layer can be implanted at a depth of less than about 4 mm and transcutaneously irradiated to effectively produce the desired photocatalytic reaction.

In some embodiments, an implant having a nitrogen-doped titania layer is implanted beneath the skin at a depth of about 3 mm, and the photocatalytic layer is irradiated with 600 nm light to produce a photocatalytic reaction that provides the ROS sufficient to destroy a biofilm located upon that photocatalytic surface.

In some embodiments, the light source is located external to the patient. Providing an external light source simplifies the design of the implant. In cases where irradiation occurs prior to the operation and the implant is still outside the patient, the light source may be a light box. In cases where irradiation occurs during the operation and the patient's wound is open, the light source may be a conventional light source, such as a flood light or the operating room lights. In cases where irradiation occurs after the operation and the patient's wound is closed, the light source can, for example, transmit light through a fiber optic cable having a proximal end connected to the light source and a distal end adapted for entry into the patient and connection to the implant as has been discussed herein.

According to some embodiments, the fiber optic cable used in conjunction with an external light source is adapted to have the strength and flexibility sufficient to navigate within the patient's tissues. For example, the fiber optic cable can be provided with a fine diameter. The proximal end of the fiber optic is adapted for connection to the light source, while the distal end of the fiber optic is adapted for connection to a waveguide or lightport disposed at the implant. Activation of the light source sends light from the light source through the fiber optic and into the implant (such as to the wave guide component of the implant).

According to some embodiments, some suitable fiber optic cable materials include quartz and silica, which are commonly available.

As shown above in FIG. 7, in some embodiments of the invention a protective delivery needle 41 or catheter can be used in conjunction with the fiber optic cable 103. The catheter has a long bore adapted to house the fiber optic and functions to protect the relatively thin fiber optic from undesired stresses encountered during navigation to the site of infection. The catheter can also serve as a protective shield that protects the surrounding tissue from any undesired effects caused by light being transmitted through the fiber optic.

According to some embodiments of the invention, so as to insure against the spread of the infection by the catheter and/or fiber optic cable, each of these components may be coated with a thin layer 51,53 of a photocatalytic material, such as titania. Irradiation of these thin layers by the light source can effectively sterilize each of these components. Further description of such a system is described supra.

In some embodiments, the light source is provided on the implant and is adapted to be permanently implanted into the patient. One advantage of such an implant comprising a light source is that when a periprosthetic infection occurs post-operatively, there is no need for further transcutaneous invasion of the patient. Rather, the internally-disposed light source is activated by, for example, a battery disposed on the implant or, for example, by a telemetry signal. In some embodiments of the present invention comprising an internal light source, the light source is provided by a bioMEMs component. In some embodiments thereof, the internal light source comprises a UV light source, and in some embodiments comprises an AlGaN substrate. It has been reported by Stutzmann, *Diamond and Related Materials*, 11 (2002) 886-891, that AlGaN may have future application as a biosensor. Stutzman further conducted studies on the biocompatibility of GaN, AlGaN and AlN, and found very little interaction with living cell tissue, thereby suggesting the biocompatibility of these materials. Accordingly, it is to be appreciated that the light source may comprise any of these materials.

In addition, in some embodiments, the bioMEMS light source may also be adapted to act as a sensor of infection. In such embodiments, the implant can function as an early detection system that can be configured to warn the clinician of a growing infection and can be used to treat the infection early.

In some embodiments, the light source is configured to produce between about 0.1 watt and 100 watts of energy. It is believed that light transmission in this energy range will be sufficient to activate the photocatalytic surface on most implants. In some embodiments, the light source is configured to produce an energy intensity at the photocatalytic surface of between 0.1 watts/cm$^2$ and 10 watts/cm$^2$. In some embodiments, the light source is configured to produce about 1 milliwatt/cm$^2$. This latter value has been reported by Ohko et al., *JBMR (Appl BioMat)* 58: 97-101, 2001, to effectively irradiate a TiO$_2$ surface in an amount sufficient to produce a photocatalytic effect. It is to also to be appreciated that the light source can be configured to produce light at power levels outside these ranges, and is contemplated by the invention.

Since photocatalytic oxidation is generally believed to be a relatively ambient-temperature process, the heat produced by both the light source transmission and the desired oxidation reactions are believed to be negligible. That is, the temperature of the tissue surrounding the implant will not generally significantly increase during activation of the PCO unit, and so the surrounding tissue will not be thermally degraded by the therapies disclosed herein.

Figure 11:
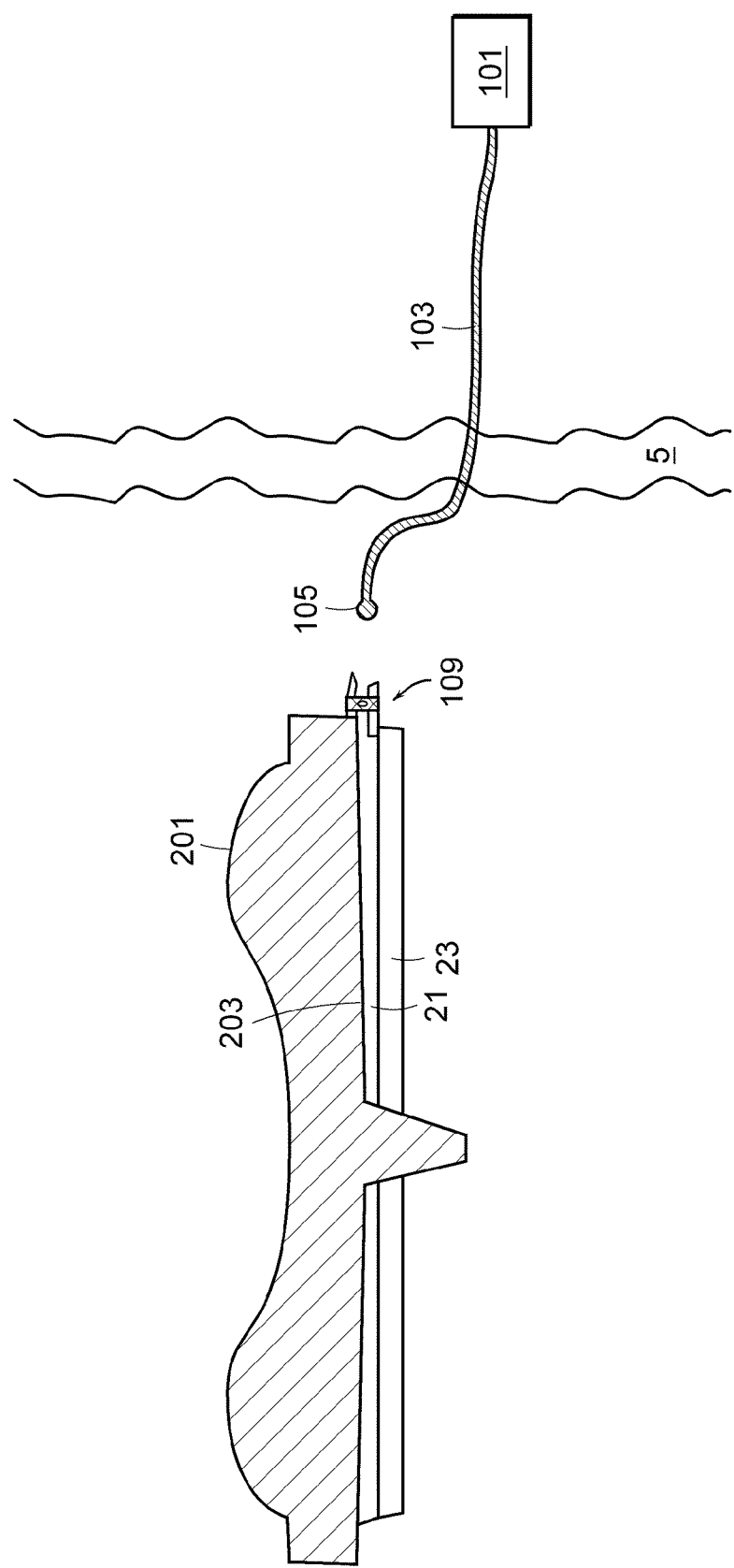
FIG. 11 is a cross-section of a photocatalytic oxidation ("PCO") unit, wherein the light source is external to the body.

Now referring to FIG. 11, there is provided an exemplary PCO unit having an external light source 101. An externally based-control device can comprise the light source 101 for providing light to the implant device, such as to an endplate of an intervertebral motion disc 201. The light generated by this source is transmitted via fiber optic cable 103 through the patient's skin S to an internally-based waveguide 21 though a light port 109 provided at the implant 201. The light port is adapted to be in light-communication with wave guide 21, to receive distal end 105 of the fiber optic and is disposed adjacent the outer surface 203 surface of the implant. A photocatalytic element 23 disposed adjacent to the wave guide receives the light from the waveguide and produces photocatalysis.

Figure 12:
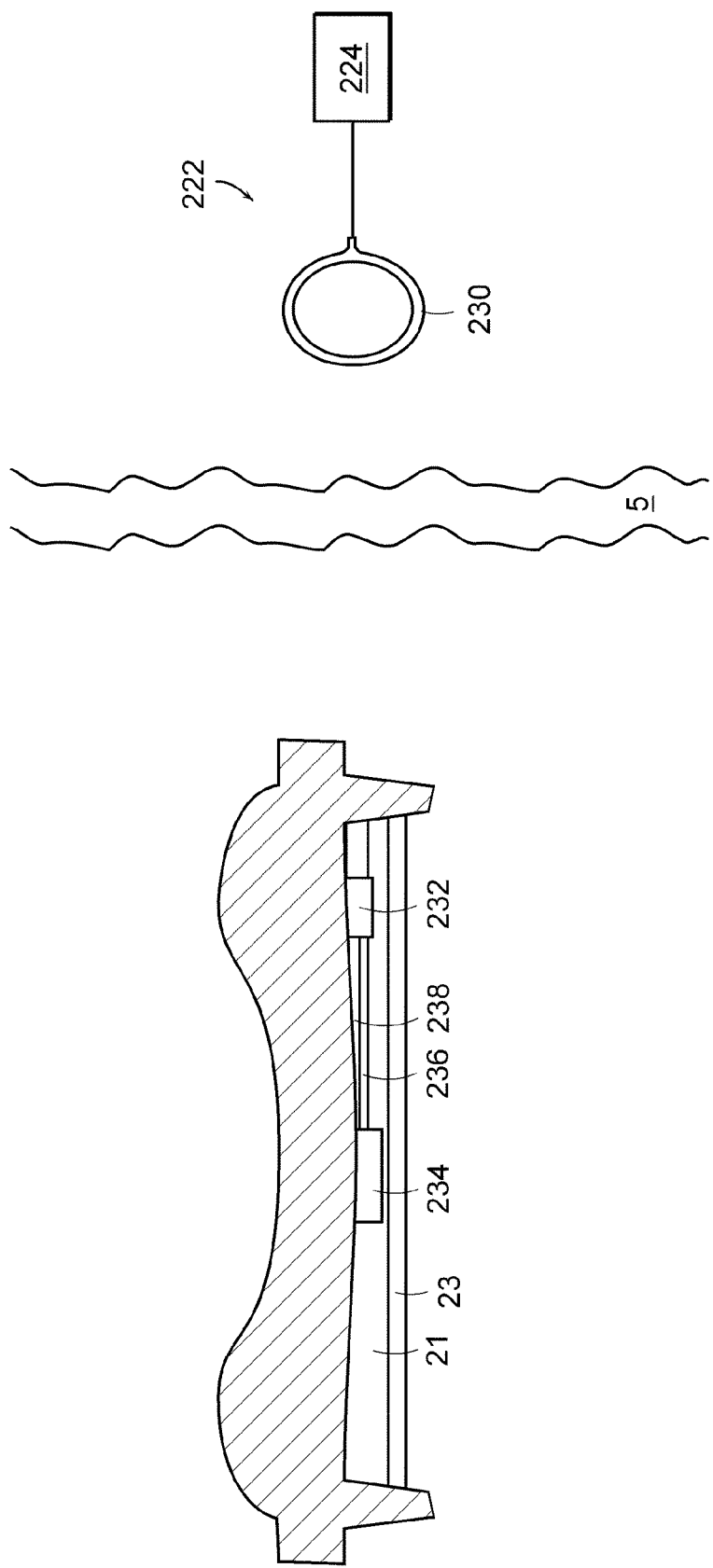
FIG. 12 is a cross-section of telemetry-powered PCO unit.

Now referring to FIG. 12, it is to be appreciated that reference numerals used herein but not specifically described, correspond to like components, layers, previously described herein, such as with respect to FIG. 11, and that for the sake of not be overly duplicitous, the description of these components is not again provided. FIG. 12 illustrates a second exemplary PCO unit having an internal light source. Externally based-control device 222 has an RF energy source 224 and an antenna 230 for transmitting signals to an internally-based antenna 232 provided on the prosthesis. These antennae 230, 232 may be electro-magnetically coupled to each other. The internal antenna 232 sends electrical power through a conductor 236 overlying an insulator 238 to a light emitting diode (LED) 234 disposed internally on the implant in response to the received signal transmitted by the external antenna 230. The light generated by the LED is coupled to and propagated by the wave guide 21 to the photocatalytic layer 23.

In some embodiments, the prosthesis may further contain an internal power source, such as a battery (not shown), which can be controlled by an internal receiver that can receive a signal to activate the battery, and the battery can be configured to have sufficient energy stored therein to deliver electrical power to the light source of the PCO unit sufficient to cause the desired photocatalytic effect.

In some embodiments, the light generated by the internal PCO unit is powered by a wireless telemetry receiver integrated onto or into the prosthetic or implant itself. In the FIG. 12 embodiment, the LED 234 may also comprise a radiofrequency-to-DC converter and modulator (not illustrated). For such an arrangement, the radiofrequency signals emitted by the antenna 230 can be picked up by the antenna 232. These signals are then converted by the receiver into electrical current to activate the light source of the PCO unit.

In some embodiments, the telemetry devices can be conventional, commercially-available components. For example, the externally-based power control device 222 can be any conventional transmitter, preferably capable of transmitting at least about 40 milliwatts of energy to the internally-based antenna 232. Examples of such commercially available transmitters are available from Microstrain, Inc. of Burlington, Vt. Likewise, the internally-based power antenna can be any conventional antenna capable of receiving and producing at least about 40 milliwatts of energy in response to coupling with the externally-generated RF signal. Examples of such commercially available antennae include those used in the Microstrain Strinlink™ device. It is to be appreciated that conventional transmitter-receiver telemetry is capable of transmitting up to about 500 milliwatts of energy to the internally-based antenna, which is also contemplated by the invention.

Figure 13:
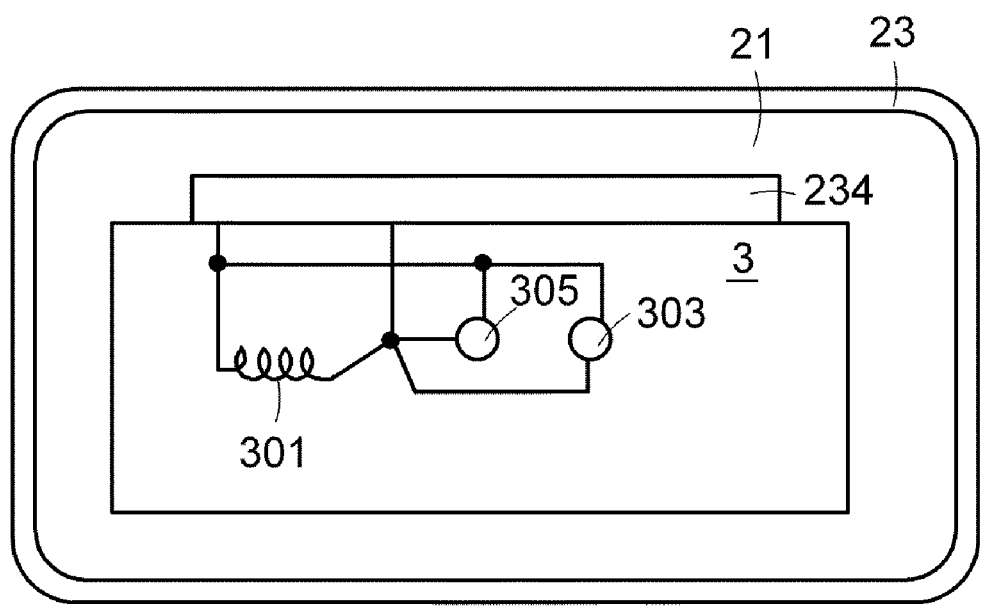
FIG. 13 is a schematic of an implant of the present invention.

In some embodiments, and now referring to FIG. 13, the implant includes a light emitting diode (LED) 234 built upon a base portion 3 of the implant, along with components to achieve trans-dermal activation and powering of the device. These components can include, but are not limited to for example, RF coils 301, control circuitry 303, a battery 305, and a capacitor (not illustrated). Such a device could be capable of intermittent or sustained activation from an external source of signal, without penetrating the skin, thereby avoiding trauma to the patient and/or risk of infection from skin-borne bacteria.

As discussed above, the accessory items used to power and control the LED may be embedded within the implant. However, they could also be located on the surface(s) of the implant, or at a site adjacent to or near the implant, and in communication with the implant, which are all contemplated by the invention.

In some embodiments, the telemetry devices of the implant can be provided by vapor depositing a metallic material upon an appropriate insulating substrate. For example, referring again to FIG. 12, the internal antenna 232 can be suitably manufactured by first creating an appropriate insulating substrate 238 upon an implant surface and then CVD depositing a metallic layer in the form of a coil upon the insulating surface.

In some embodiments, it may be desirable to locate the light source, associated controller, power and telemetry components at a location separate from the implant, and provide a light communication device between the two sites. The light communication device may include, for example, any of a fiber optic cable, a wave guide, a hollow tube, a liquid filled tube, and a light pipe. Such a configuration would allow the implant to be located deep within the patient, or in or near critical organs or tissues, and yet have the light source and associated components in a less sensitive region. This configuration allows easier access to the light/controller should the need arise for service or maintenance, and also allows for more efficient transdermal energy transmission. Moreover, by using a hollow tube with reflective internal surfaces as the light transmission device, light and also therapeutic fluids could be delivered to the implanted device. The light source/controller implanted near the patient's skin could also be a simple, hollow chamber made to facilitate the percutaneous access as has been described above. Some advantages and benefits of this system include:

- further removal from the deep site of the light source/controller of the functional implant, thereby reducing risk of contamination of the deeper site by percutaneous access;
- easier precutaneous access to the light source/controller by being closer to the skin surface and having a larger surface area or target to access with the needle;
- a larger volume reservoir of the light source/controller could hold more therapeutic fluid to provide a longer duration of activity; and
- such a remote controller could serve as a central reservoir to provide therapeutic fluids to multiple implants throughout the body.

In some embodiments, the photocatalytic capabilities of the implant device of the present invention may be supplemented with an adjunct system for treating a periprosthetic infection. One such system comprises a pharmaceutical delivery system. In some embodiments, the pharmaceutical delivery system is a coating comprising a pharmaceutical, wherein the coating is disposed upon a surface of the implant. This coating acts as a sustained release device for the pharmaceutical that insures a constant introduction of the pharmaceutical into the surrounding tissue.

In some embodiments, an implant comprising the pharmaceutical coating is disposed within a porous scaffold adapted to interface with a bony surface. This embodiment not only places the pharmaceutical at a location highly susceptible to infection, but also insures that the physical integration between the implant and the bony surface will not be compromised when the coating eventually disappears.

In some embodiments, pharmaceutical delivery system comprises a drug pump containing a pharmaceutical. The drug pump can be activated either at the end of the surgery or afterward to provide a constant introduction of the pharmaceutical into the surrounding tissue.

In some embodiments, the pharmaceutical delivery system comprises at least one channel created within or on the surface of an implant for delivering the pharmaceutical to a plurality of locations about the implant surface. According to some embodiments, the channel is fully enclosed by the implant and defines an entry port (adapted for receiving a needle) located upon a first surface of the implant and at least one exit port opening onto a second surface of the implant. It is to be appreciated that according to such embodiments, when a plurality of channels and exit ports extend from the same entry port, a pharmaceutical can be injected into the entry port of the implant and carried through the channels to the plurality of exit ports. With this arrangement, the pharmaceutical can be spread over the surface adjacent the exit ports in an amount effective to provide a beneficial effect. In some embodiments, the channels can comprise porous material.

Figure 14:
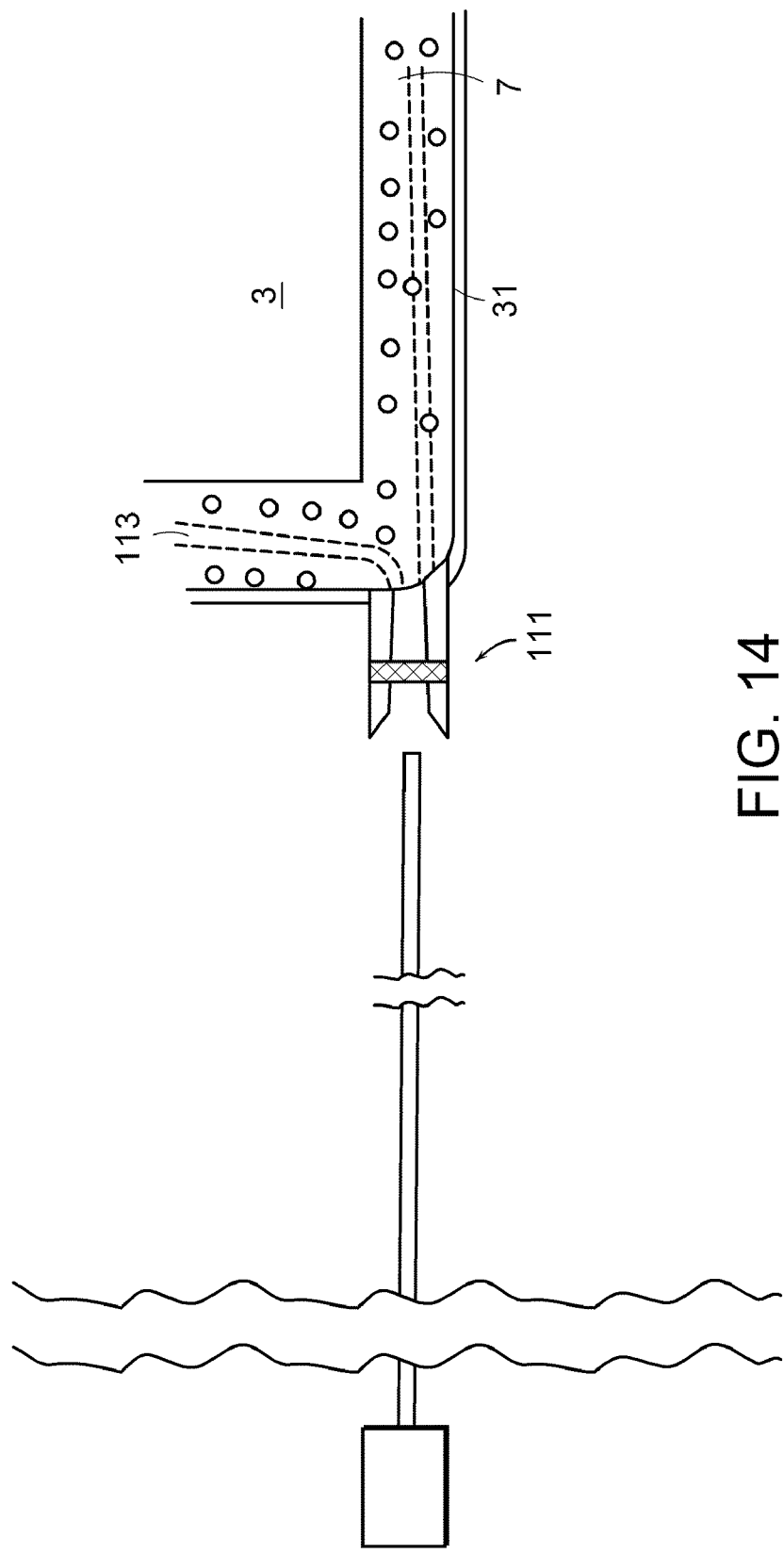
FIG. 14 is a cross-section of an implant having an apparatus for delivering fluids.

Now referring to FIG. 14, in some embodiments of the present invention, there is provided an implant having a base material 3, a porous photocatalytic intermediate layer 7, an outer reflective (e.g., silver) coating layer 31, and a fluid delivery device 111 for delivering fluids to the implant. The device for delivering fluids 111 can be the same structure used as a light port, discussed herein, thereby providing the implant with two functions in the same structure. According to such embodiments, the fluid delivery device is capable of infusing a desired fluid over the entire surface of the device. This can be accomplished by the use of the porous layer 7 (e.g., a plasma sprayed titanium layer as is commonly used on orthopedic implant). In some embodiments, a porous channel 113 (shown by dotted lines) can be built into the porous layer to provide a more even distribution of the fluid throughout the porous layer. In some embodiments, the porous layer can also function as the light waveguide and photocatalytic layer as has been discussed supra.

It is to be appreciated that the porous nature of the intermediate layer 7 provides for bony ingrowth, while the photocatalytic nature of this layer provides for antimicrobial activity upon post-surgical irradiation. In addition, the outer reflective coating 31 layer provides both desirable reflection of light back into the photocatalytic layer and immediate antimicrobial activity without any further post-surgical intervention.

In some embodiments, the pharmaceutical is selected from the group consisting of an antibiotic, a growth factor and an anti-inflammatory. In such embodiments, the antibiotic can be delivered to the adjacent tissue in an amount effective to prevent a periprosthetic infection. Suitable antibiotics are desirably delivered in conventional prophylactic concentrations. In such embodiments, the growth factor can be delivered into the adjacent tissue in an amount effective to enhance bony in-growth into the porous layer, thereby securing attachment of the implant to the adjacent bone. In such embodiments, the anti-inflammatory can be delivered to the adjacent tissue in an amount effective to antagonize pro-inflammatory cytokines, and thereby prevent bone loss. Suitable anti-inflammatories include anti-TNF-α compounds and anti-interleukin-1μcompounds. Specific desirable compounds include (Remicade™).

According to some embodiments, the pharmaceutical delivery system comprises a silver halide coating. It is believed that the silver component of this coating becomes ionized following dissolution. Once ionized, it can enter the cellular membrane of adjacent microbes and promote an intra-cellular reaction that produces singlet oxygen. It is believed that the singlet oxygen so produced has a lethal effect upon the invaded cell. In one embodiment thereof, the silver halide coating can also be used as a reflective coating adjacent a wave guide.

In some embodiments, hydrogen peroxide can be delivered through the fluid delivery mechanisms discussed herein, to be present in the vicinity of the photocatalytic layer. It has been reported in U.S. Pat. No. 4,861,484 ("Lichtin") that hydrogen peroxide has a significant synergistic effect upon the titania-based photocatalysis. For example, Lichtin reports that the destruction of certain organic compounds proceeds about 5-10 times as rapidly when titania is irradiated in the presence of hydrogen peroxide (as compared to its destruction rate when titania irradiated without hydrogen peroxide). Accordingly, it is believed that the provision of hydrogen peroxide with the present invention may enhance the effectiveness of the desired photocatalytic activity.

In some embodiments, a photosensitizer can be delivered through the fluid delivery mechanisms discussed herein, to be present in the vicinity of the photocatalytic layer. It has been reported by Wainright, *J. Antimicrobial Chemotherapy*, (1998) 42, 13-28, that local irradiation of photosensitizers (such as methylene blue) should be considered as a mechanism for treating local infection due to their ability to produce singlet oxygen. Accordingly, it is believed that the additional provision of photosensitizers with the present invention may enhance the effectiveness of the desired photocatalytic activity. In some embodiments, the photosensitizer is selected from the group consisting of phenothiazinium type, phenazine type, acridine type, cyanine type, porphyrin type, phthalocyanine type, psoralen type, and perylenequinonoid type.

In some embodiments, a luminescent compound can be delivered through the fluid delivery mechanisms discussed herein, to be present in the vicinity of the photocatalytic layer. It is known that certain luminescent materials such as luminol can react with other reactants to produce light. Luminol is of particular interest in that the light produced from its reactions is about 424 nm. This 424 nm light should be effective to produce the excitation of some of the doped titania discussed above. Accordingly, it may be possible to produce the required light around an infected implant without the need for an invasive fiber optic cable. Accordingly, it is believed that the provision of providing a luminescent compound in accordance with some embodiments of the present invention may enhance the effectiveness of the desired photocatalytic activity. In some embodiments, the photosensitizer is selected from the group consisting of bioluminescent and chemiluminescent compounds.

Figure 15:
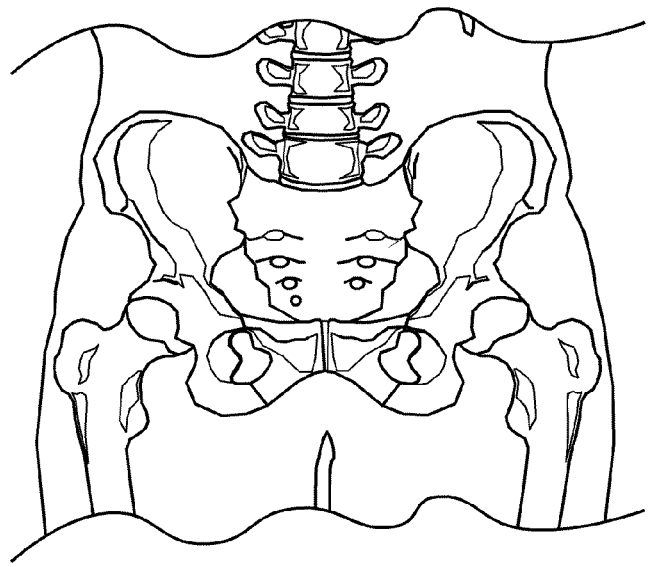
FIG. 15 is a cross-section of a hip implant of the present invention.

Now referring to FIG. 15, in some embodiments, the PCO unit is provided upon a hip prosthetic. In some embodiments, a photocatalytic layer 1501 is provided upon a surface 1503 of the base material 1502 located upon the femoral stem of the implant. As shown in FIG. 15, the photocatalytic layer is preferably encased in a reflective layer 1505. Preferably, each of these layers is porous and is suitable as a porous scaffold for bony ingrowth. In other embodiments, the photocatalytic layer is provided upon a surface located upon the femoral head (not shown) of the implant. In some embodiments, the photocatalytic layer is provided upon a surface located upon the acetabular cup (not shown) of the implant. In some embodiments, the prosthetic further has a light port (not shown) to facilitate illumination of the photocatalytic surface.

Figure 16:
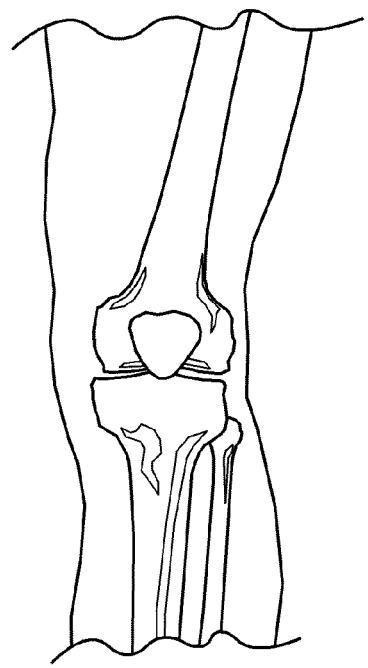
FIG. 16 is a cross-section of a knee implant of the present invention.

Now referring to FIG. 16, in some embodiments, the PCO unit is provided upon a knee prosthetic 1601 such as illustrated in FIG. 16. In some embodiments, thereof, a photocatalytic layer 1603 is provided upon a surface 1602 of a base material 1604, and is substantially encased in a reflective layer 1605. According to some embodiments, each of these layers is porous, is suitable as a porous scaffold for bony ingrowth, and is provided upon a surface adapted to contact bone. According to some embodiments, the prosthetic further has a light port (not shown) to facilitate illumination of the photocatalytic surface.

Figure 17:
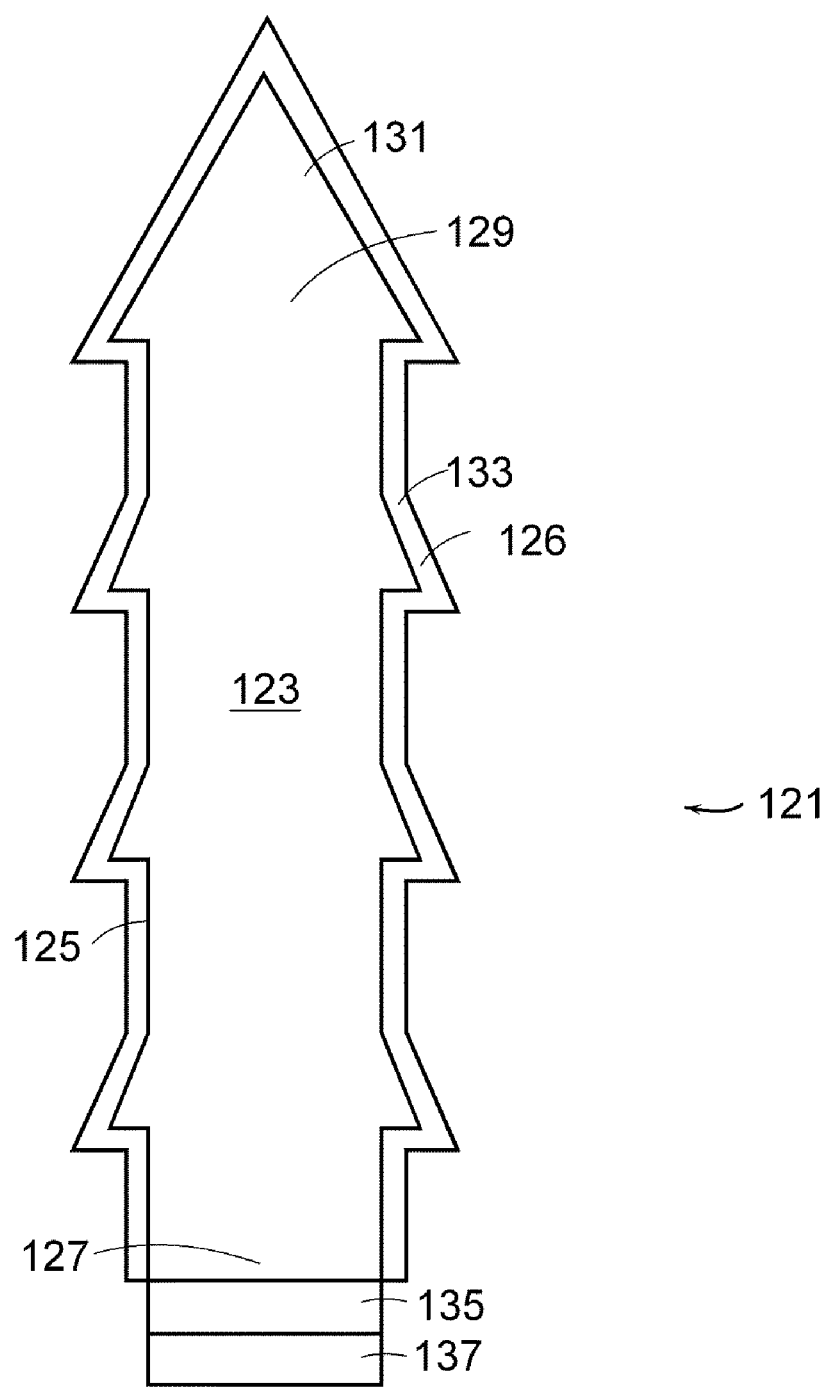
FIG. 17 is a cross-section of a screw implant of the present invention.

In some embodiments, a bone screw is provided with a photocatalytic surface. For example, now referring to FIG. 17, in some embodiments a bone screw 121 comprises a body portion 123 made from a light transmissible material (such as single crystal sapphire), an outer surface 125 at least a portion of which is threaded 126, a proximal portion 127, a distal portion 129 containing a narrow head portion 131, a photocatalytic surface 133 disposed upon the outer surface of the screw, a light source 135 (such as an LED) disposed upon the proximal portion of the screw, and an antenna 137 in electrical connection with the light source. It is to be appreciated that in some embodiments of the bone screw, the LED and antenna can be replaced with a light port, and the light source can be externally based.

In some embodiments, the PCO unit is provided upon a spinal prosthetic. In some embodiments, thereof, it is provided upon a motion disc. In some embodiments it is provided upon a scoliosis correction system. In some embodiments it is provided upon an intervertebral fusion device.

Figure 18:
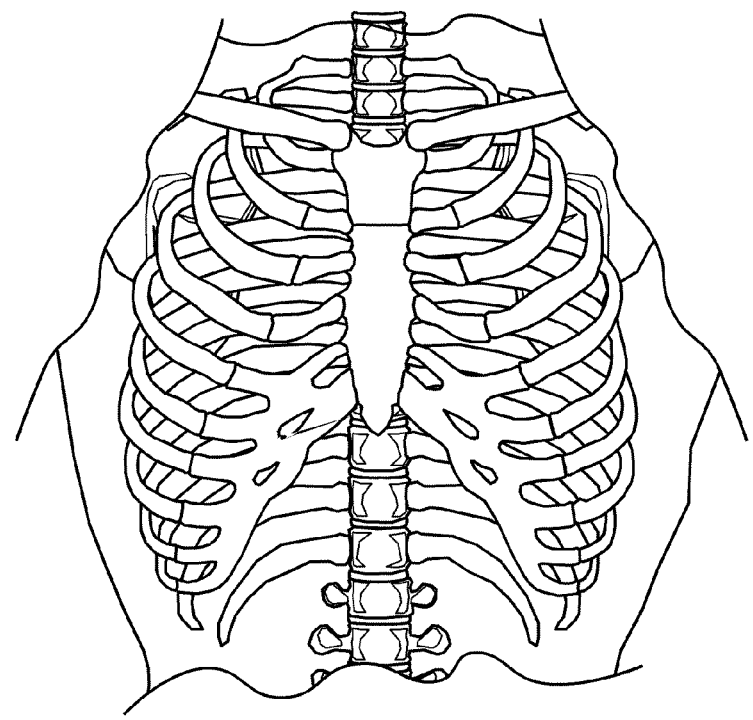
FIG. 18 is a cross-section of an Intervertebral Fusion implant of the present invention.

For example, now referring to FIG. 18, in some embodiments, an intervertebral fusion device 1801 is provided with the photocatalytic surface 1803. In some embodiments, a photocatalytic layer 1803 is a composite layer comprising a wave guide, as has been discussed herein, and the photocatalytic material. The photocatalytic layer 1803 is provided upon at least one of upper and lower bearing surfaces 1805 of the fusion device. In some embodiments, thereof, the photocatalytic layer 1803 is substantially encased in a reflective layer 1807. According to some embodiments, each of these layers is porous and is suitable as a porous scaffold for bony ingrowth. According to some embodiments, the prosthetic may also have a light port 1809 to facilitate illumination of the photocatalytic surface. In other embodiments, the photocatalytic surface is provided upon at least one internal surfaces of the fusion device (not illustrated).

Figure 19:
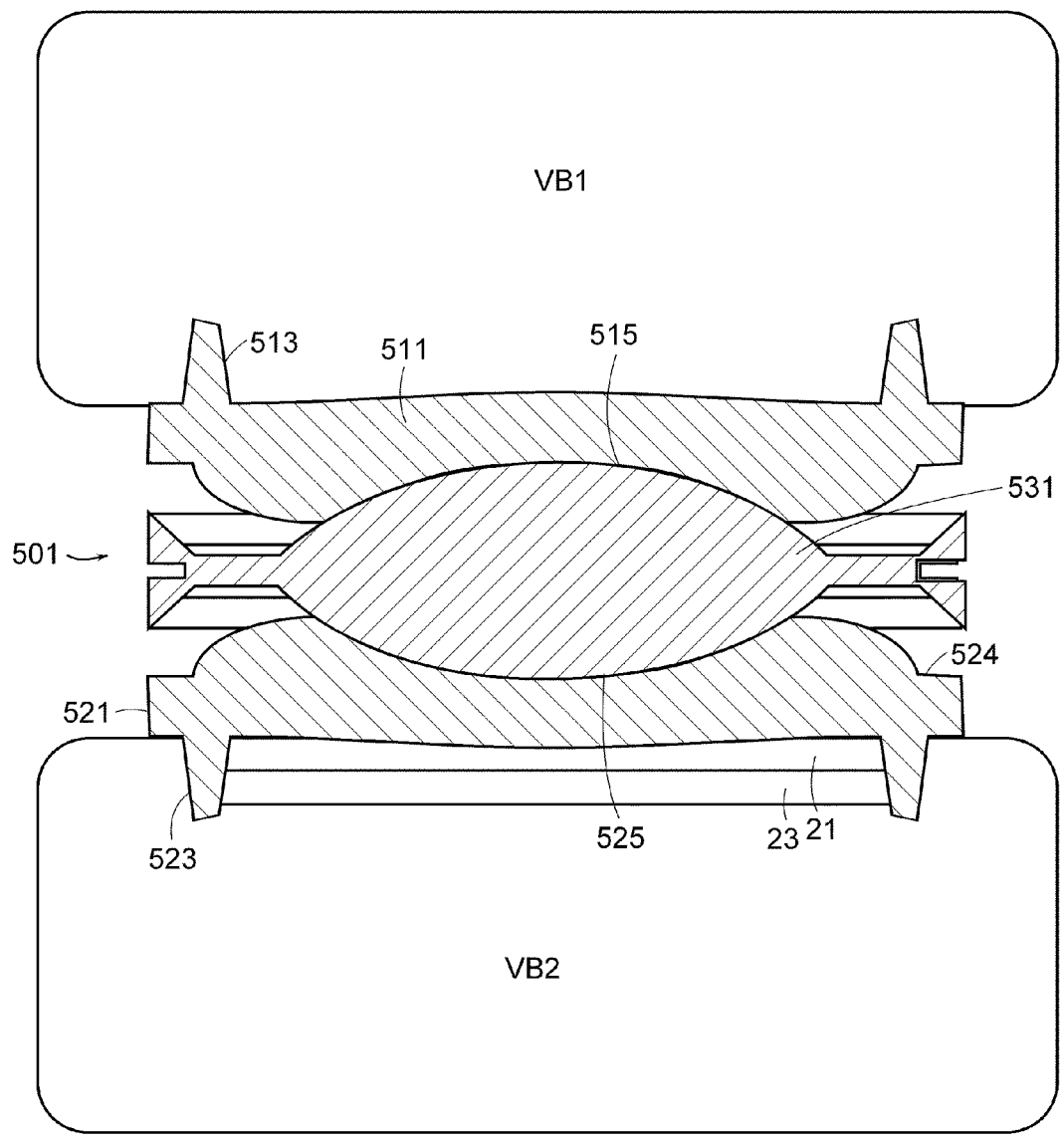
FIG. 19 is a cross-section of an intervertebral motion disc implant of the present invention.

Now referring to FIG. 19, the PCO unit can be provided upon an intervertebral motion disc 501. According to some embodiments, the motion disc is selected from the group consisting of a cushion disc and an articulating disc. In some embodiments, the articulating disc 501 comprises a first prosthetic vertebral endplate 511 comprising an outer surface 513 adapted to mate with a first vertebral body VB1, and an inner surface comprising a first articulation surface 515 suitable for supporting articulation motion. The articulating disc also comprises a second prosthetic vertebral endplate 521 comprising an outer surface 523 adapted to mate with a second vertebral body VB2, and an inner surface 524 comprising a second articulation surface 525 suitable for supporting articulation motion. As shown in FIG. 19, some embodiments comprise a wave guide 21 that overlies outer surface 523, and a photocatalytic layer 23 overlies the wave guide. A light port or an LED (neither shown) may be placed in light communication with the wave guide, as has been discussed herein.

In some embodiments, the motion disc is a two-piece design (wherein the articulation surfaces of the prosthetic endplates are adapted to form an articulation interface). In others, the motion disc is a three-piece design further including a core (wherein opposed articulation surfaces of the core are adapted to form two articulation interfaces with the corresponding articulation surfaces of the prosthetic endplates).

It is known that scoliosis correction systems are associated with a higher than normal rates of infection. Therefore, in some embodiments, at least one component of the PCO unit is provided upon a spinal deformity unit. In some cases, the bone screw of the spinal deformity unit is provided with the photocatalytic surface as has been discussed herein, for example, with respect to FIG. 17. In some embodiments, a rod component of the spinal deformity unit is provided with the photocatalytic surface.

Figure 20:
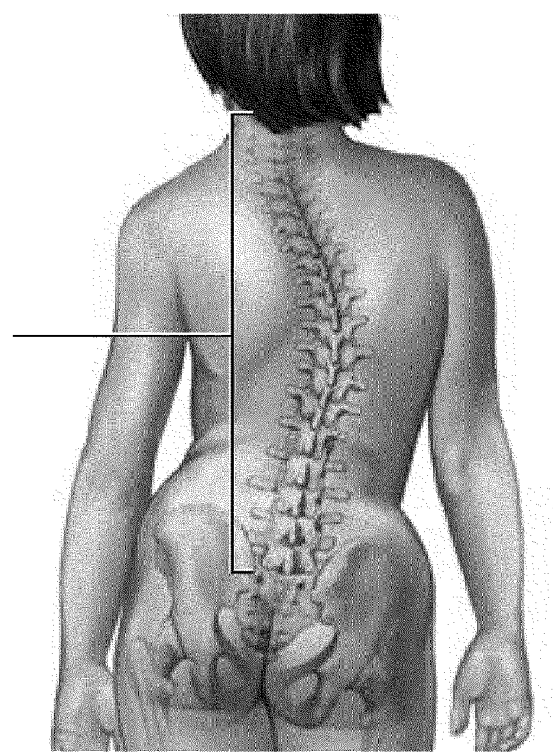
FIG. 20 is a cross-section of a spinal deformity correction unit of the present invention.

For example, now referring to FIG. 20, a cross-connector component 2001 of the spinal deformity unit is provided with a photocatalytic layer 2003. In the illustrated embodiment, nuts 2008 hold the cross-connector to the screws 2009. In some embodiments, the photocatalytic layer 2003 of FIG. 20 is a composite layer comprising the wave guide and the photocatalytic material as discussed herein. The photocatalytic layer 2003 is provided upon at least one of the inner 2004 and outer 2005 surfaces of the base material of the cross-connector that faces the tissue. In some embodiments, thereof, the photocatalytic layer 2003 is substantially encased in a reflective layer 2007. According to some embodiments, each of these layers is porous and is suitable as a porous scaffold for bony ingrowth. According to some embodiments, the prosthetic further has a light port 1809 (See FIG. 18) to facilitate illumination of the photocatalytic surface.

Figure 21:
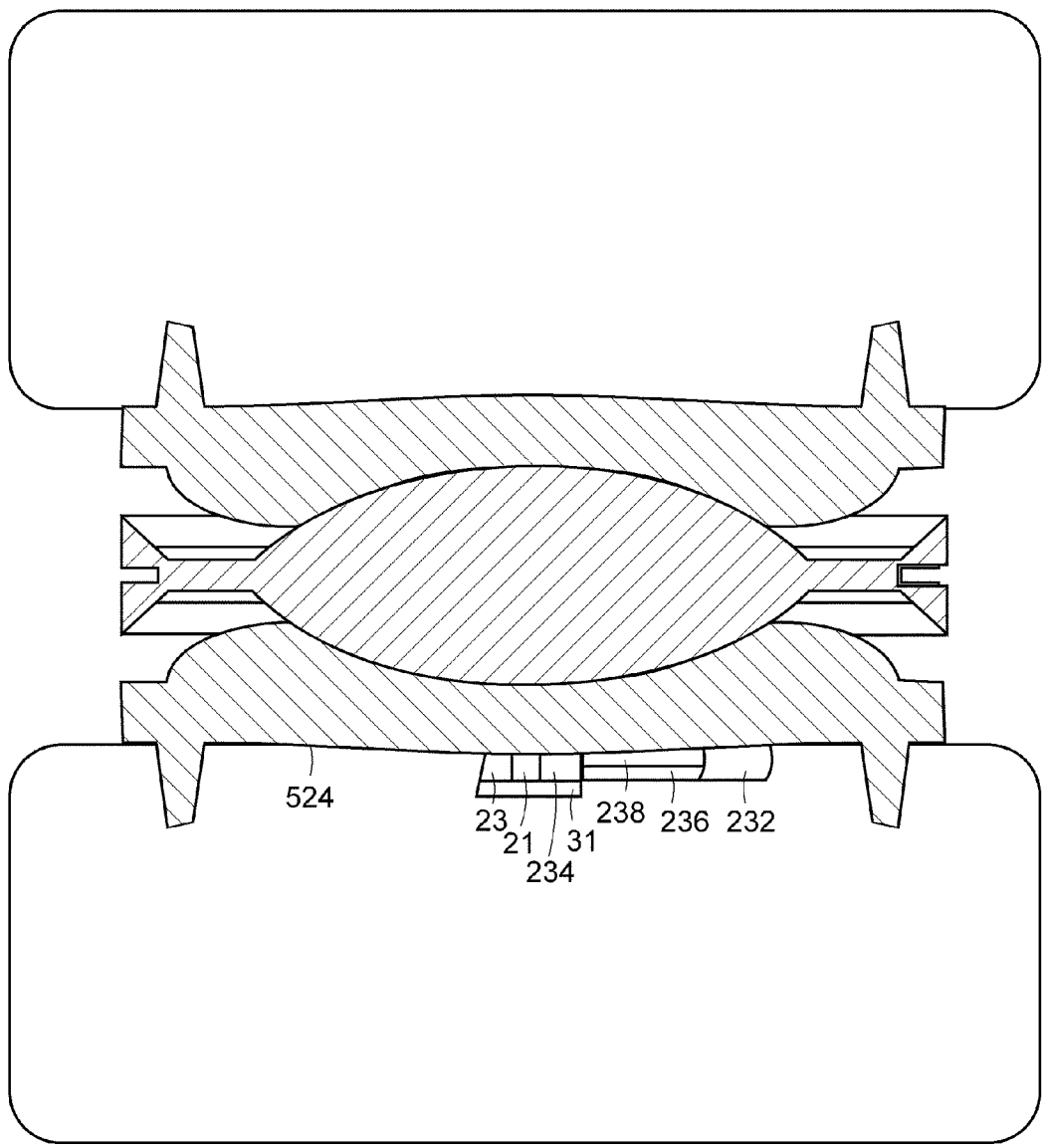
FIG. 21 is a cross-section of a device of the present invention wherein both the light source and an antenna are provided on the outer surface of the implant at the implant-bone interface.

Now referring to FIG. 21, it is to be appreciated that like reference numerals used herein but not specifically described, correspond to like components, layers, previously described herein, such as with respect to FIGS. 12 and 19, and that for the sake of not be overly duplicitous, the description of these components is not again provided. In some embodiments, the PCO unit can be located upon a bone in-growth surface such as surface 550 of the prosthetic implant. In this embodiment, the photocatalytic layer 23 is in light communication with the LED 234 via wave guide 21, thereby obviating depth of UV penetration concerns as has been discussed herein. This embodiment also has an advantage of providing all of the PCO components on the same surface, thereby allowing for ease of manufacturing by a CVD process. Moreover, when the PCO unit is so situated, the activated species produced thereby quickly engage any bacteria present at the point of the wound.

Figure 22:
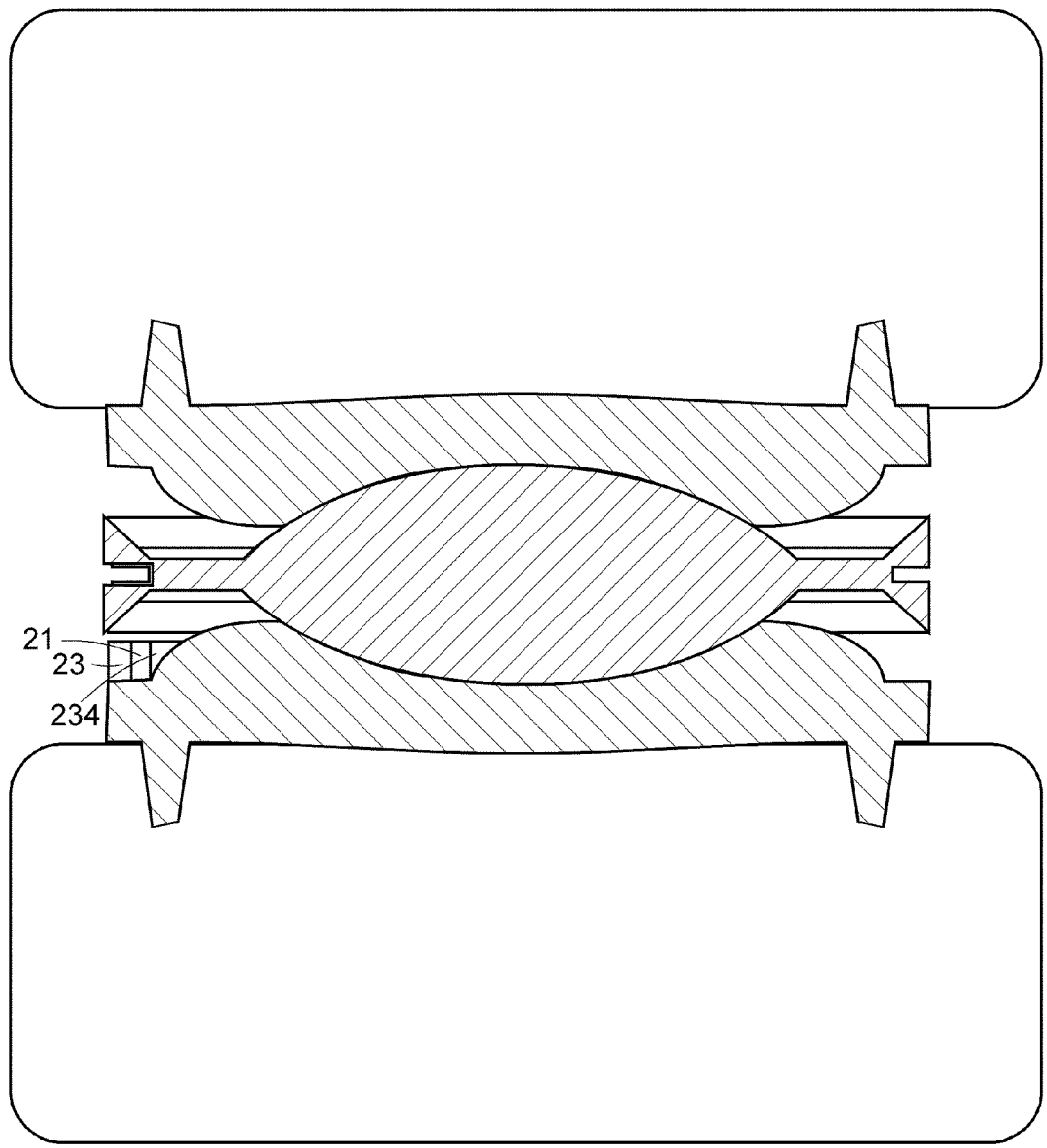
FIG. 22 is a cross-section of a device of the present invention wherein both the light source and the antenna are provided on an inner surface of the implant.

Now referring to FIG. 22, it is to be appreciated that reference numerals used herein but not specifically described, correspond to like components, layers, previously described herein, such as with respect to FIGS. 12, and 19-21, and that for the sake of not be overly duplicitous, the description of these components is not again provided. In addition, it is to be appreciated that for the sake of simplicity, like parts have not all been labeled with reference numbers. In some embodiments, the LED 234 can be located upon an inner surface 524 of the prosthetic implant, and the photocatalytic layer 23 is in light communication with the LED 234 via wave guide 21. This embodiment has a mechanical advantage in that when the PCO unit is so situated, it is likely subjected to less stresses and so it electrical connections are less likely to fail.

Figure 23:
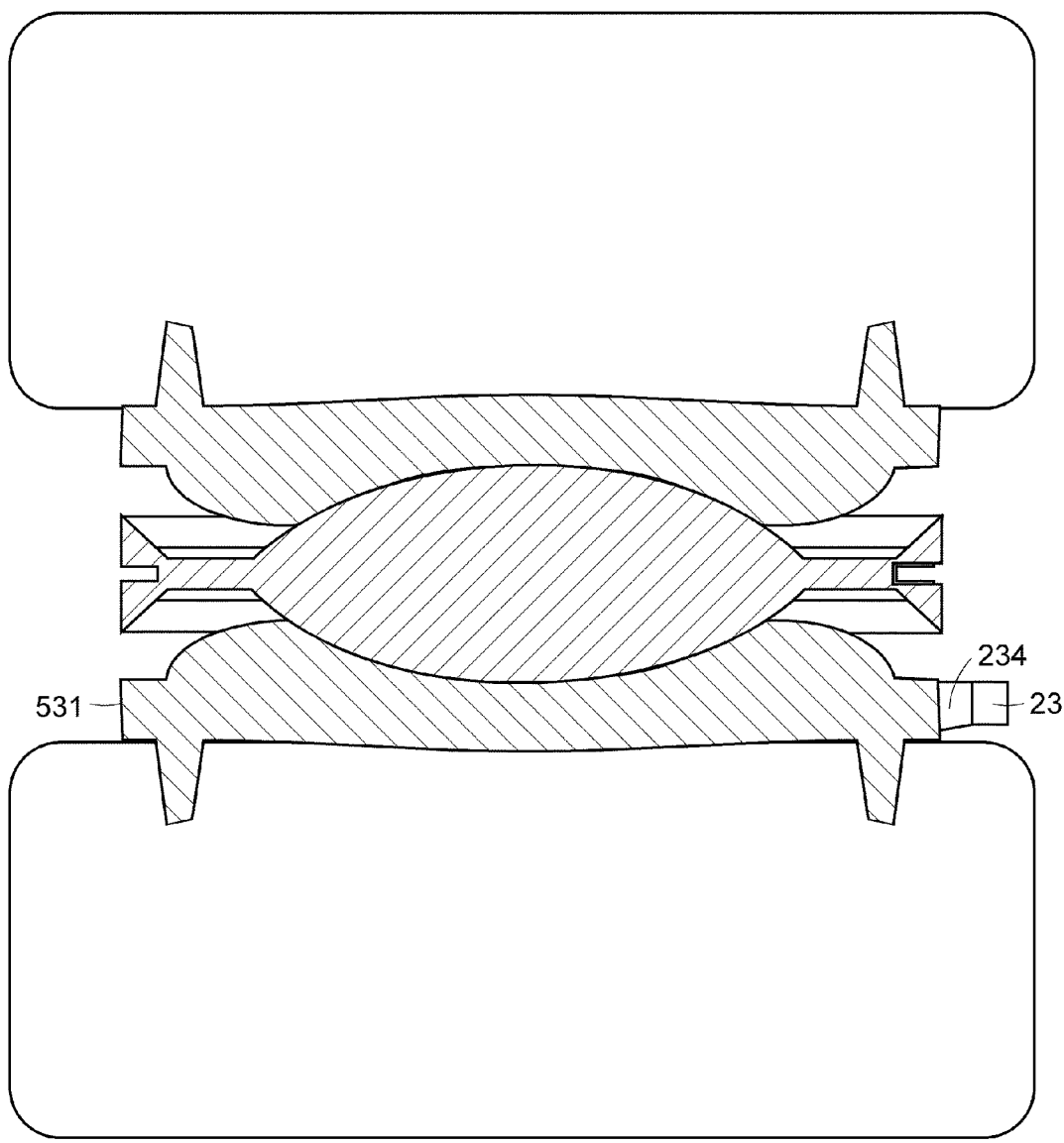
FIG. 23 is a cross-section of a device of the present invention wherein both the light source and the photocatalytic layer are provided on the rim of the implant.

Now referring to FIG. 23, it is to be appreciated that reference numerals used herein but not specifically described, correspond to like components, layers, previously described herein, such as with respect to FIGS. 12, and 19-22, and that for the sake of not be overly duplicitous, the description of these components is not again provided. In addition, it is to be appreciated that for the sake of simplicity, like parts have not all been labeled with reference numbers. In some embodiments, the LED 234 can be located upon a peripheral rim surface 552 of the prosthetic implant. This embodiment has an advantage that, when the PCO unit is so situated, and the infection occurs at a point of internal sutring, the activated species produced by the quickly engage peripheral bacteria located in that sutre.

Figure 24:
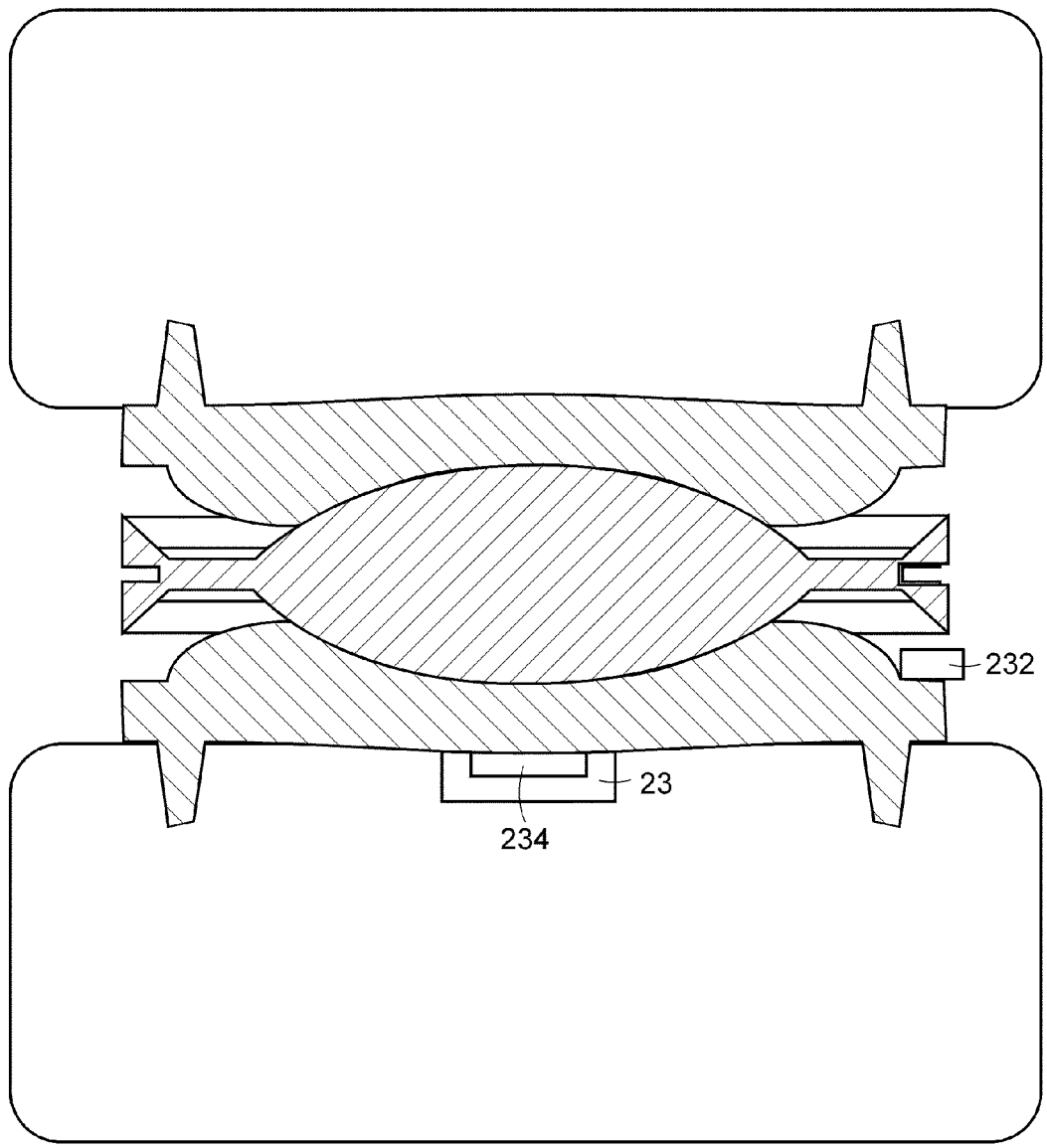
FIG. 24 is a cross-section of a device of the present invention wherein the light source is provided on an outer surface of the implant at the implant-bone interface and the antenna is provided on an inner surface.

Now referring to FIG. 24, it is to be appreciated that reference numerals used herein but not specifically described, correspond to like components, layers, previously described herein, such as with respect to FIGS. 12, and 19-23, and that for the sake of not be overly duplicitous, the description of these components is not again provided. In addition, it is to be appreciated that for the sake of simplicity, like parts have not all been labeled with reference numbers. In some embodiments, the LED 234 of the PCO unit can be located upon a bone in-growth surface 550 of the prosthetic implant, while the antenna 232 can be located upon another surface such as the inner surface 524. This embodiment has an advantage that the PCO unit is in proximity to the bacteria present at the point of the wound, and the remote placement of the antenna does not interfere with the UV penetration of the bone-prosthetic interface.

Figure 25:
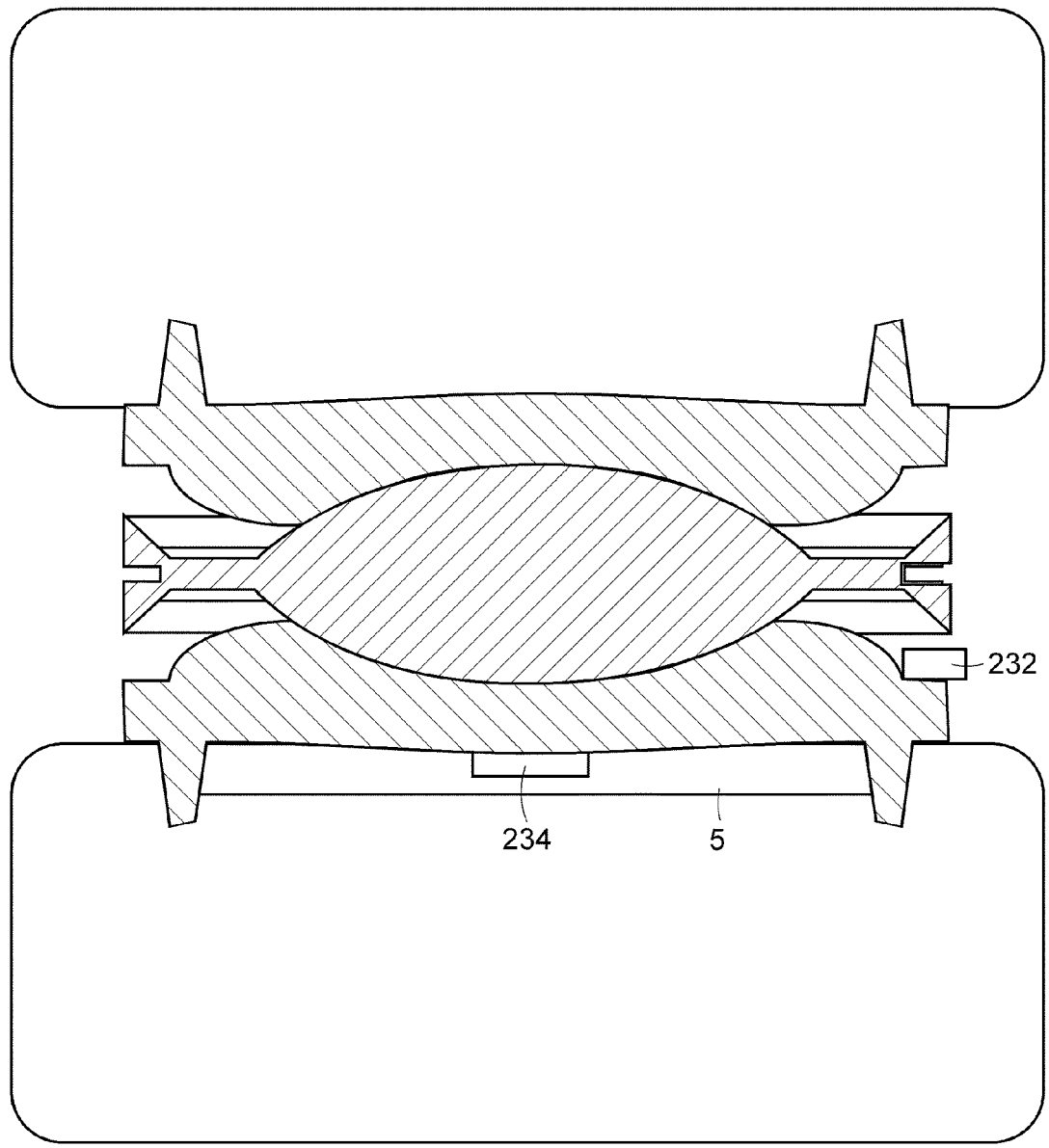
FIG. 25 is a cross-section of a device of the present invention wherein a titanium-containing surface of the implant is oxidized to produce a photocatalytic surface.

Now referring to FIG. 25, it is to be appreciated that reference numerals used herein but not specifically described, correspond to like components, layers, previously described herein, such as with respect to FIGS. 12, and 19-24, and that for the sake of not be overly duplicitous, the description of these components is not again provided. In addition, it is to be appreciated that for the sake of simplicity, like parts have not all been labeled with reference numbers. In some embodiments, the photocatalytic layer 5 can be produced by oxidizing a titanium-containing surface of a Ti alloy implant. The oxidation of the surface of a titanium alloy implant can be carried out by the teachings of Trepanier, discussed supra. One advantage of such embodiment is that the photocatalytic layer spreads across substantially the entire lower surface of the implant, and is situated precisely at the often-problematic bone-implant interface 550.

Figure 26:
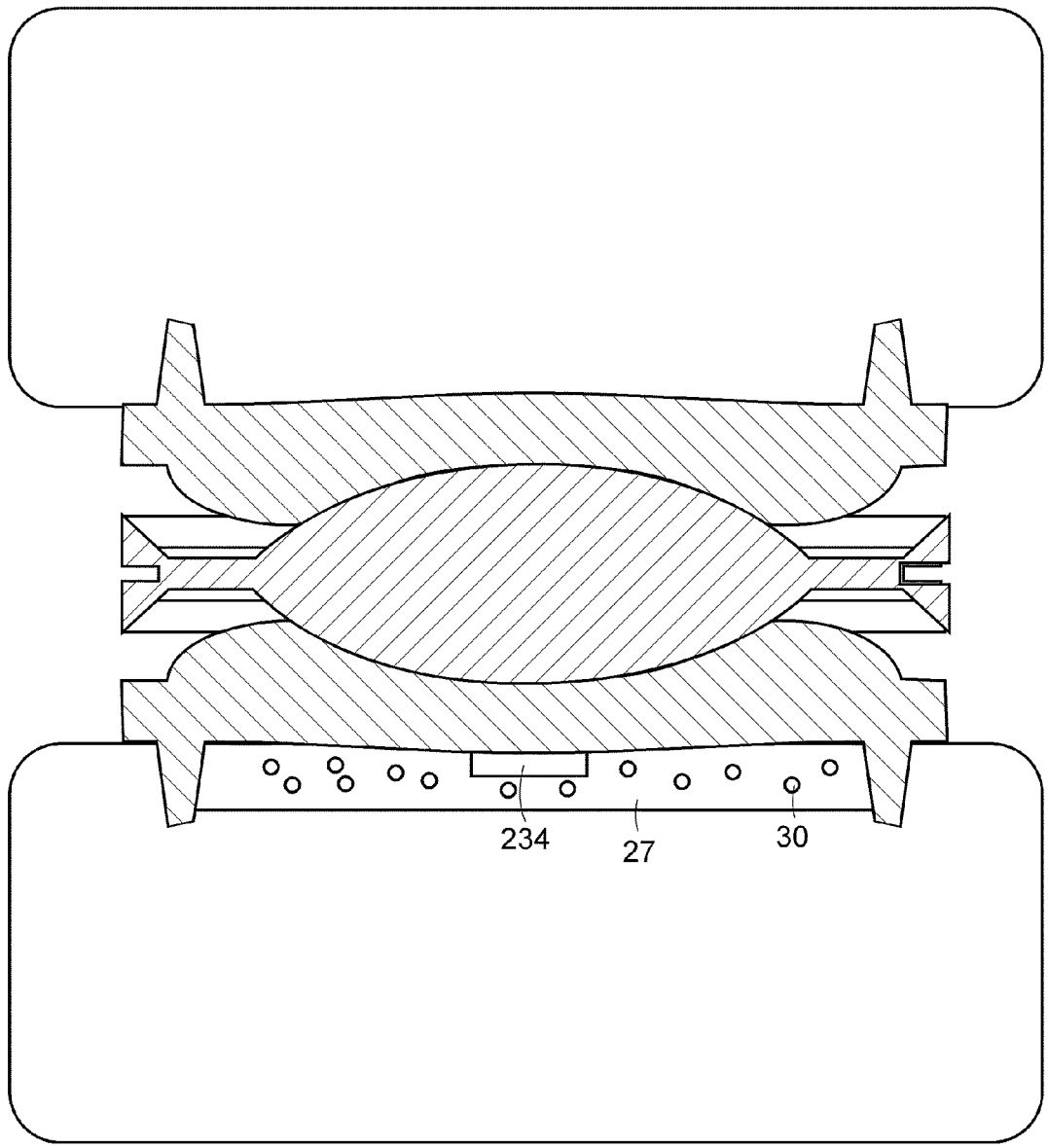
FIG. 26 is a cross-section of a device of the present invention wherein a porous scaffold containing titanium dioxide is applied to a surface of the implant to produce a photocatalytic surface.

Now referring to FIG. 26 it is to be appreciated that reference numerals used herein but not specifically described, correspond to like components, layers, previously described herein, such as with respect to FIGS. 12, and 19-25, and that for the sake of not be overly duplicitous, the description of these components is not again provided. In addition, it is to be appreciated that for the sake of simplicity, like parts have not all been labeled with reference numbers. In some embodiments, the photocatalytic layer 27 comprises porosity 30 to provide a porous scaffold suitable for bone growth. For example, a porous scaffold of titania film can be manufactured as described above. Some advantages of such embodiment of an implant device are that the porous $TiO_2$ portion of the device provides two functions. First, the porous nature of this scaffold allows for bony ingrowth. Second, the UV sensitive nature of the $TiO_2$ material allows its irradiation by LED 234 to produce ROS capable of disinfecting the entire porous scaffold.

Figure 27:
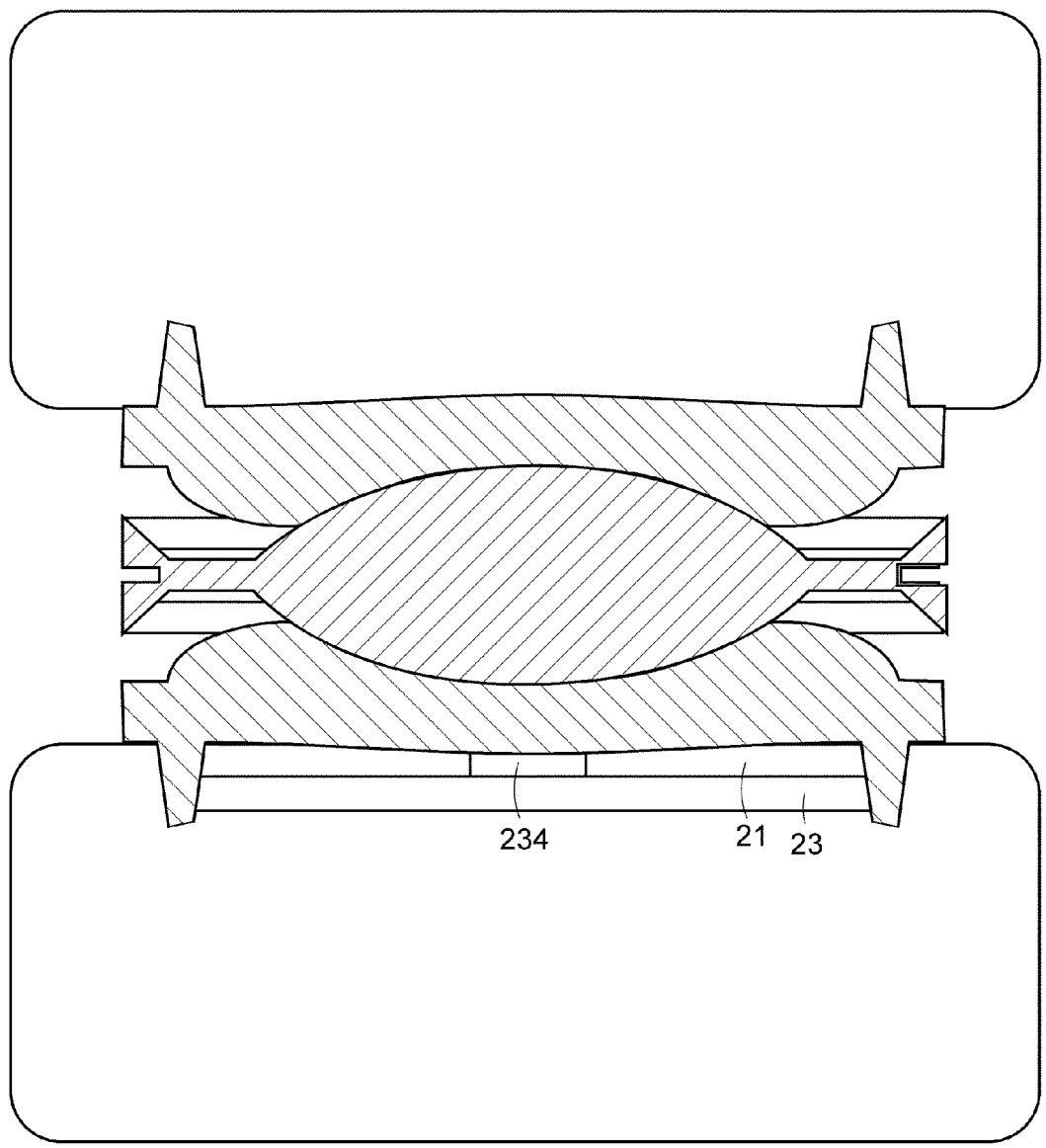
FIG. 27 is a cross-section of a device of the present invention wherein a wave guide is placed adjacent an LED to diffuse the light from its source.

Now referring to FIG. 27, it is to be appreciated that reference numerals used herein but not specifically described, correspond to like components, layers, previously described herein, such as with respect to FIGS. 12, and 19-26, and that for the sake of not be overly duplicitous, the description of these components is not again provided. In addition, it is to be appreciated that for the sake of simplicity, like parts have not all been labeled with reference numbers. According to this embodiment, there is provided a device of the present invention in which the LED 234 is centrally located on the outer surface of the implant, for example, at the bone-implant interface 550 and is surrounded by a UV transmissible material forming a wave guide 21. Some exemplary suitable UV-transmissible materials include alumina, silica and sapphire. A porous scaffold comprising TiO2 overlays the UV-transmissible peripheral layer and forms the photocatalytic layer 23. One advantage of this embodiment of the implant device is that the UV transmissible material acts as a wave guide, so that the UV light generated from the LED can spread laterally across the surface of the implant and thereby irradiate the titania in the porous scaffold over the entire surface.

Figure 28:
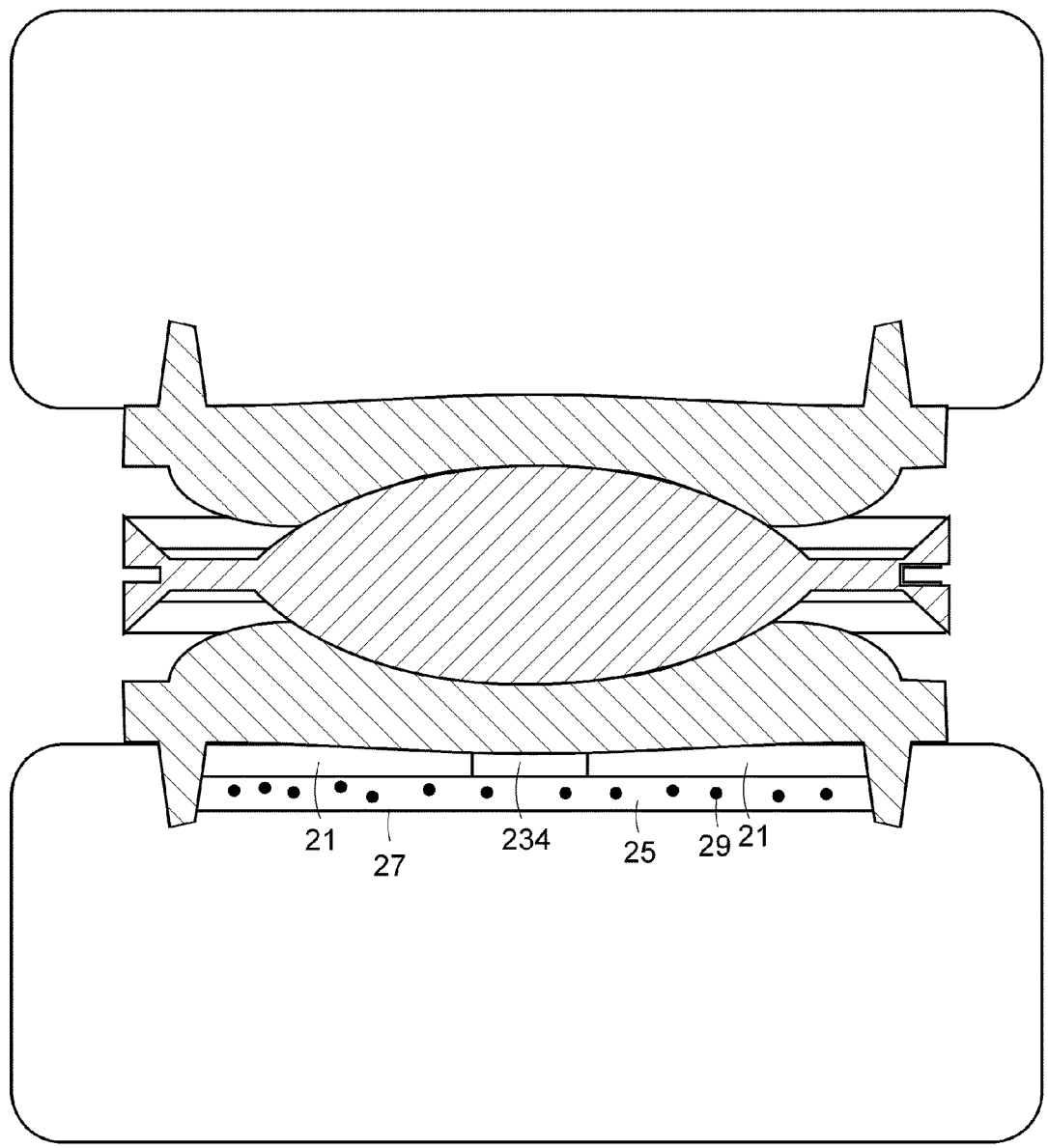
FIG. 28 is a cross-section of a device of the present invention wherein the implant has a porous scaffold comprising a UV transmissible material and a semiconductor material.
Figure 29:
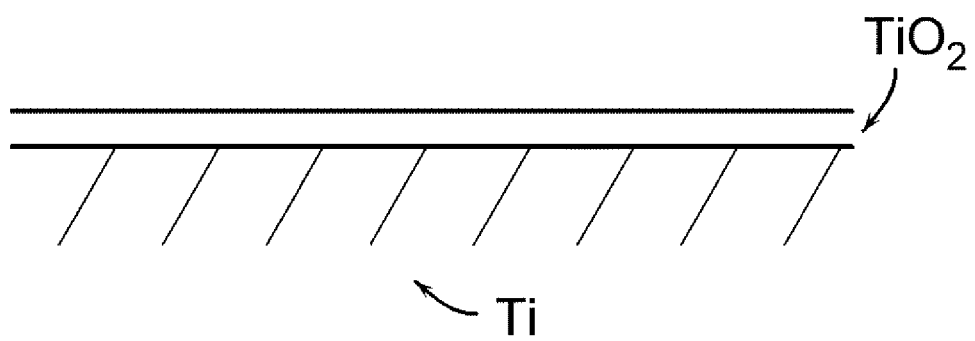
FIG. 29 is a prior art representation of a periprosthetic infection.

Now referring to FIG. 28, it is to be appreciated that reference numerals used herein but not specifically described, correspond to like components, layers, previously described herein, such as with respect to FIGS. 12, and 19-27, and that for the sake of not be overly duplicitous, the description of these components is not again provided. In addition, it is to be appreciated that for the sake of simplicity, like parts have not all been labeled with reference numbers. According to this embodiment, there is provided a device of the present invention wherein the porous scaffold comprises both a first wave guide 21 and a composite layer 27 comprising the semiconductor material 29 and a light-transmissible (for example, UV-transmissible) material 25. It is to be appreciated that this embodiment as well as each of these embodiments can be provided so as to have the properties and advantages that have been discussed herein with respect to other embodiments comprising these layers and components.

In other embodiments, the LED and antenna components disclosed with respect to the above described embodiments, can be replaced by a wave guide light receiving port. With such an arrangement, an externally-disposed fiber optic can be inserted into the patient, connected to the wave guide port, and activated as has been discussed supra.

It is to be appreciated that in some instances, the implant can be subject to therapeutic photocatalytic treatment prior to its implantation. Pre-implantation treatment is a preventative measure that can provide the surgeon with extra assurance that the implant is sterile when it enters the body. For example, providing a pre-implantation photocatalysis can also reduce the risk that transmissible diseases such as mad cow disease and AIDS become problematic.

In some pre-implantation embodiments thereof, an implant can be placed in an aqueous slurry of titania particles and photoenergy can be applied to provide the slurry to produce the photocatalysis. The ROS produced by the photocatalysis will oxidize not only any bacteria attached to the implant, but also problematic spores. It has been reported by Wolfrum, *Environ. Sci. Tech.*, 2002, 36, 3412-19 that a titania-based reactor exposed to about 10 mW/cm$^2$ of 365 nm light is sufficient to kill *A. niger* spores.

It is to be appreciated that photocatalysis can also be provided upon the implant intra-operatively (i.e., during the surgery). For example, just prior to closing the patient, the surgeon can use a fiber optic to irradiate the photocatalyzable surface of the implant, thereby insuring that any bacteria that became attached to the implant during the surgery will be rendered ineffective. It is believed that a substantial percentage of problematic PPIs arise from infection occurring at the interface of the patient's bone and the implant, and that such an arrangement can be used to mitigate such PPIs.

Therefore, in some embodiments, the implant of the present invention is implanted into the patient and the PCO unit is then activated during the surgery. In some embodiments, the PCO unit activation occurs immediately prior to closing up the patient.

In some embodiments, the PCO unit activation occurs immediately after closing up the patient. For example, the patient can be closed with the fiber optic still attached to the wave guide port. The surgeon then uses the fiber optic to irradiate the photocatalyzable surface of the implant, thereby insuring that any bacteria that became attached to the implant during the surgery will be rendered ineffective. After irradiation, the fiber optic is drawn from the patient.

In some embodiments, the herein described PCO procedures can be configured to effectively act upon the target bacteria colony to eliminate at least 50% of the colony, preferably at least 90%, and more preferably at least 99%. In some embodiments, the ROS generated by the PCO unit are provided so as to be present in the reaction zone is an amount effective to sterilize the reaction zone. The sterilization of the reaction zone means that spores in addition to bacteria are killed. In some embodiments, the PCO procedure can be configured to effectively essentially completely oxidize the target bacteria to carbon dioxide and water.

In some embodiments, the ROS generated by the PCO unit can be provided in the reaction zone is an amount effective to disinfect the reaction zone. Typically bacteria that are considered to be prone to photocatalysis include, but are not limited to, *staphylococcus epidermis*. Microbes involved in mad cow disease and AIDS are also contemplated to be within the scope of the system and method for treating infections of the present invention. *Staphylococcus epidermis* is thought to be introduced into the patient through the normal flora of the skin. As has been discussed herein, these types of bacteria tend to form a biofilm on the surface of the implant, which can be eliminated by the herein described methods and apparatus of the invention.

It is to be appreciated that although the above discussion has focused upon providing photocatalytic devices for treating or preventing infection, the present inventors believe that photocatalytic implants may also be used to treat other non-infection conditions. For example, a cardiovascular stent may be designed to possess a photocatalytic unit that photooxidizes cells within inflamed intimal tissue involved in the local inflammatory process caused by deployment of a stent, thereby preventing restenosis. In another example, a tubular device housing a needle may be adapted for peripheral photooxidation of the cells involved in the local inflammation caused by invasion from the needle, thereby preventing FOP. In another example, a device may be adapted for peripheral photooxidation of the cells and particles involved in the local inflammation caused by wear debris involving small UHMWPE particles, thereby preventing osteolysis.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of some embodiments of the present invention. Accordingly, the foregoing description and drawings are by way of example only.

We claim:

1. A medical implant comprising:
   a) photocatalytic surface, and
   b) a light source adapted to irradiate the photocatalytic surface with light in an amount sufficient to activate photocatalysis thereon, wherein the implant is adapted to act as a sensor.

2. The implant of claim 1 wherein the sensor comprises the photocatalytic surface.

3. The implant of claim 1 wherein the sensor comprises the light source.

4. The implant of claim 3 wherein the sensor comprises a detection system.

* * * * *